US010954265B2

(12) United States Patent
Xu et al.

(10) Patent No.: US 10,954,265 B2
(45) Date of Patent: Mar. 23, 2021

(54) STRUCTURES AND MECHANISM FOR THE DESIGN OF HIGHLY POTENT GLUCOCORTICOIDS

(71) Applicant: Van Andel Research Institute, Grand Rapids, MI (US)

(72) Inventors: Huaqiang Eric Xu, Grand Rapids, MI (US); Yuanzheng He, Grand Rapids, MI (US)

(73) Assignee: VAN ANDEL RESEARCH INSTITUTE, Grand Rapids, MI (US)

( * ) Notice: Subject to any disclaimer, the term of this patent is extended or adjusted under 35 U.S.C. 154(b) by 0 days.

(21) Appl. No.: 16/341,275

(22) PCT Filed: Oct. 13, 2017

(86) PCT No.: PCT/US2017/056447
§ 371 (c)(1),
(2) Date: Apr. 11, 2019

(87) PCT Pub. No.: WO2018/071736
PCT Pub. Date: Apr. 19, 2018

(65) Prior Publication Data
US 2019/0263853 A1 Aug. 29, 2019

Related U.S. Application Data

(60) Provisional application No. 62/408,314, filed on Oct. 14, 2016.

(51) Int. Cl.
| | |
|---|---|
| *C07J 71/00* | (2006.01) |
| *A61P 11/06* | (2006.01) |
| *A61P 19/02* | (2006.01) |
| *A61P 37/06* | (2006.01) |
| *A61P 17/10* | (2006.01) |
| *A61P 1/00* | (2006.01) |

(52) U.S. Cl.
CPC ............ *C07J 71/0047* (2013.01); *A61P 11/06* (2018.01); *A61P 19/02* (2018.01); *A61P 37/06* (2018.01); *A61P 1/00* (2018.01); *A61P 17/10* (2018.01)

(58) Field of Classification Search
CPC .................................................... C07J 71/0047
See application file for complete search history.

(56) References Cited

U.S. PATENT DOCUMENTS

| | | | |
|---|---|---|---|
| 4,049,813 | A | 9/1977 | Nadelson |
| 4,086,421 | A | 4/1978 | Nadelson |
| 7,087,756 | B2 | 8/2006 | Hintermann et al. |
| 8,163,724 | B2 | 4/2012 | Bladh et al. |
| 8,173,670 | B2 | 5/2012 | Xu et al. |

| | | | |
|---|---|---|---|
| 2010/0256105 | A1 | 10/2010 | Burkamp et al. |
| 2012/0178726 | A1* | 7/2012 | Bladh ................. C07J 71/0047 514/170 |
| 2016/0251393 | A1 | 9/2016 | Xu et al. |

FOREIGN PATENT DOCUMENTS

| | | | |
|---|---|---|---|
| EP | 1408042 A1 | 4/2004 | |
| WO | 2009044200 A1 | 4/2009 | |
| WO | 2010083218 A1 | 7/2010 | |
| WO | 2010114471 A1 | 10/2010 | |
| WO | 2010114476 A1 | 10/2010 | |
| WO | 2010147947 A1 | 12/2010 | |
| WO | WO2010147947 | * 12/2010 | |
| WO | 2015048316 A1 | 4/2015 | |

OTHER PUBLICATIONS

Bishop et al., Nonsurgical Therapy for Solitary Rectal Ulcer Syndrome. Current Treatment Options in Gastroenterology, vol. 5, pp. 215-223 (Year: 2002).*
U.S. Appl. No. 15/024,496, filed Sep. 25, 2014, U.S. Pat. No. 9,975,918, Badio, Barbara P, Issued.
Adcock, I. M., et al. (1999) Ligand-induced differentiation of glucocorticoid receptor (GR) trans-repression and transactivation: preferential targetting of NF-kappaB and lack of I-kappaB involvement. Br J Pharmacol 127 (4):1003-1011.
Bailey, S. (1994) The Ccp4 Suite—Programs for Protein Crystallography. Acta Crystallogr D 50:760-763.
Barnes, P J (1998) Anti-inflammatory actions of glucocorticoids: molecular mechanisms. Clin Sci (Loud) 94 (6):557-572.
Barnes, P. J., et al. (2009) Glucocorticoid resistance in inflammatory diseases. Lancet 373 (9678):1905-1917.
Baxter, J. D. (1976) Glucocorticoid hormone action. Pharmacol Ther B 2 (3):605-669.
Biggadike, K., et aL (2008) X-ray crystal structure of the novel enhanced-affinity glucocorticoid agonist fluticasone furoate in the glucocorticoid receptor-ligand binding domain. J Med Chem 51 (12):3349-3352.
Bledsoe, R. K., et al. (2002) Crystal structure of the glucocorticoid receptor ligand binding domain reveals a novel mode of receptor dimerization and coactivator recognition. Cell 110 (1):93-105.
Brunger, A. T., et al (1998) Crystallography & NMR system: A new software suite for macromolecular structure determination. Acta Crystallogr D Biol Crystallogr 54 (Pt 5):905-921.
Crim, C., et al. (2001) A review of the pharmacology and pharmacokinetics of inhaled fluticasone propionate and mometasone furoate. Clin Ther 23 (9):1339-1354.
De Bosscher, K. et al. (2003) the interplay between the glucocorticoid receptor and nuclear factor-kappaB or activator protein-1: molecular mechanisms for gene repression. Endocr Rev 24 (4):488-522.
Frey, F. J., et al. (2004) Glucocorticoid-mediated mineralocorticoid receptor activation and hypertension. Curr Opin Nephrol Hypertens 13 (4):451-458.

(Continued)

*Primary Examiner* — Barbara P Badio
(74) *Attorney, Agent, or Firm* — Honigman LLP; Douglas H. Siegel; Jonathan P. O'Brien

(57) ABSTRACT

The present invention relates to novel glucocorticoid compounds. The invention also relates to methods of using these compounds, the synthesis of these compounds, and to compositions and formulations comprising the glucocorticoid compounds, and uses thereof.

10 Claims, 21 Drawing Sheets

(56) References Cited

OTHER PUBLICATIONS

Figure 1A:
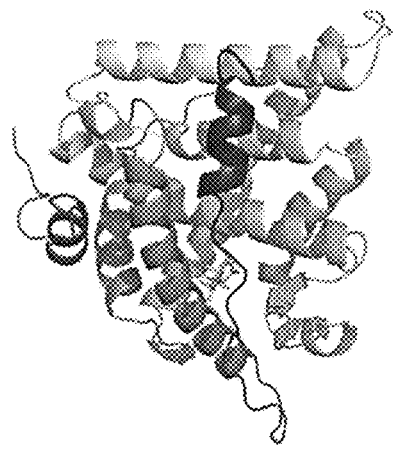
Figure 1A:
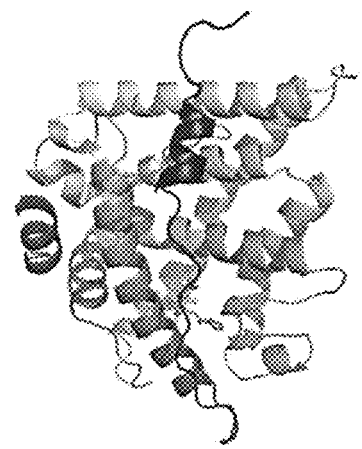

Gaynon, P. S., et al. (1999) Glucocorticosteroid therapy in childhood acute lymphoblastic leukaemia. Adv Exp Med Biol 457:593-605.

Haarman, E. G., et al. (2003) Glucocorticoid resistance in childhood leukaemia: Mechanisms and modulation. Brit J Haematol 120 (6):919-929.

Harmon, J. M., et al. (1982) Non-glucocorticoid receptor-mediated effects of the potent glucocorticoid deacylcortivazol. Cancer Res 42 (6):2110-2114.

He, Y., et al. (2011) Identification of a lysosomal pathway that modulates glucocorticoid signaling and the inflammatory response. Sci Signal 4 (180):ra44.

Heck, S., et al. (1994) A distinct modulating domain in glucocorticoid receptor monomers in the repression of activity of the transcription factor AP-1. EMBO J 13 (17):4087-4095.

Hoes, J. N., et al. (2009) Adverse events of low-to medium-dose oral glucocorticoids in inflammatory diseases: a meta-analysis. Ann Rheum Dis 68 (12):1833-1838.

Hoes, J. N., et al. (2010) Current view of glucocorticoid co-therapy with DMARDs in rheumatoid arthritiS. Nat Rev Rheumatol 6 (12):693-702.

Kaspers, G. J., et al. (1994) Glucocorticoid resistance in childhood leukemia. Leuk Lymphoma 13 (3-4):187-201.

Kauppi, B., et al. The three-dimensional structures of antagonistic and agonistic forms of the glucocorticoid receptor ligand-binding domain: RU-486 induces a transconformation that leads to active antagonism. J. Biol Chem 2003; 278:22748-22754.

Lefstin, J. A., et al. (1998) Allosteric effects of DNA on transcriptional regulators. Nature 392 (6679):885-888.

McCormack, P. L., et al. (2006) Inhaled mometasone furoate: A review of its use in persistent asthma in adults and adolescents. Drugs 66 (8):1151-1168.

Murshudov, G. N., et al. (1997) Refinement of macromolecular structures by the maximum-likelihood method. Acta Crystallogr D Biol Crystallogr 53 (Pt 3):240-255.

Nakae, J., et al. (2001) The forkhead transcription factor Foxo1 (Fkhr) confers insulin sensitivity onto glucose-6-phosphatase expression. J Clin Invest 108 (9):1359-1367.

Onrust, S. V., et al. (1998) Mometasone furoate. A review of its intranasal use in allergic rhinitis. Drugs 56 (4):725-745.

Opherk, C., et al. (2004) Inactivation of the glucocorticoid receptor in hepatocytes leads to fasting hypoglycemia ameliorates and hyperglycemia in streptozotocin-induced diabetes mellitus. Mol Endocrinol 18 (6):1346-1353.

Pinzone, J. J., et al. (2009) The role of Dickkopf-1 in bone development, homeostasis, and disease. Blood 113 (3):517-525.

Reichardt, H. M., et al. (1998) DNA binding of the glucocorticoid receptor is not essential for survival. Cell 93 (4):531-541.

Rosen, J., et al. (2005) The search for safer glucocorticoid receptor ligands. Endocr Rev 26 (3):452-464.

Schacke, H., et al. (2002) Mechanisms involved in the side effects of glucocorticoids. Pharmacal Ther 96 (1):23-43.

Simons, S. S. (2003) The importance of being varied in steroid receptor transactivation. Trends in Pharmacological Sciences24 (5):253-259.

Simons, S. S., Jr. (2006) How much is enough? Modulation of dose-response curve for steroid receptor-regulated gene expression by changing concentrations of transcription factor. Curr Top Med Chem 6 (3):271-285.

Simons, S. S., Jr. (2008) What goes on behind closed doors: physiological versus pharmacological steroid hormone actions. Bioessays 30 (8):744-756.

Spies, C. M., et al. (2011) Glucocorticoids. Best Pract Res Cl Rh 25 (6):891-900.

Stanbury, R. M., et al. (1998) Systemic corticosteroid therapy—side effects and their management. Br J Ophthalmol 82 (6):704-708.

Suino-Powell, K, et al. (2008) Doubling the size of the glucocorticoid receptor ligand binding pocket by deacylcortivazol. Mol Cell Biol 28 (6):1915-1923.

Wei, P., et al. (1998) Modulation of hormone-dependent glucocorticoid receptor function using a tetracycline-regulated expression system. Journal of Steroid Biochemistry and Molecular Biology 64 (1-2):1-12.

Williams, S. P., et al. (1998) Atomic structure of progesterone complexed with its receptor. Nature 393 (6683):392-396.

Jan. 4, 2018 ISR and Written Opinion for PCT/US17/56447; 12 pages.

PubMed Compound Summary for CID 88584815, 'Schembl 10276628', U.S. National Library of Medicine, Feb. 13, 2015, 11 Pages [https://pubchem.ncbi.nlm.nih.gov/compound/88584815].

Extended European Search Report for EP Application No. 17860202.5 dated Mar. 31, 2020, 12 pages.

Alangari, A.A. Genomic and non-genomic actions of glucocorticoids in asthma. Ann Thorac Med. 2010; 5 (3):133-139.

Allen, A., et al. Fluticasone Furoate, A Novel Inhaled Corticosteriod, Demonstrates Prolonged Lung Absorption Kinetics in Man Compared with Inhaled Fluticasone Propionate. Clin Pharmacokinet (2013) 52:37-42.

Barker, M., et al. Dissociated Nonsteroidal Glucocorticoid Receptor Modulators; Discovery of the Agonist Trigger in a Tetrahydronaphthalene-Benzoxazine Series. J. Med. Chem. 2006, 49, pp. 4216-4231.

Biggadike, K., et al. "Design and x-ray crystal structures of high-potency nonsteroidal glucocorticoid agonists exploiting a novel binding site on the receptor." Proceedings of the National Academy of Sciences 106.43 (2009) 18114-18119.

Buttgereit, F., et al. Optimised glucocorticoid therapy: the sharpening of an old spear. Lancet 2005; 365:801-803.

Coghlan, M.J., et al. A Novel Antiinflammatory Maintains Glucocorticoid Efficacy with Reduced Side Effects. Mol Endocrinol, May 2003; 17(5):860-869.

Costantino, G., et al. Unbinding pathways from glucocorticoid receptor shed light on reduced sensitivity of glucocorticoid ligands to a naturally occurring, clinically relevant, mutant receptor. Journal of medicinal chemistry (2013), 56, pp. 7003-7014.

De Bosscher, K., et al. Minireview: Latest Perspectives on Antiinflammatory Actions of Glucocorticoids. Mol Endocrinol, Mar. 2009, 23(3):281-291.

Mar. 22, 2017 Supplementary Partial European Search Report for EP14849674; 25 pages.

Dewint, P., et al. A Plant-Derived Ligand Favoring Monomeric Glucocorticoid Receptor Conformation with Impaired Transactivation Potential Attenuates Collagen-Induced Arthritis. The Journal of Immunology 2008; 180:2608-2615.

Ernst, P., et al. Systemic effects of inhaled corticosteriods. Curr Opin Pulm Med 2012, 18:85-89.

He, Y., et al. Structures and mechanism for the design of highly potent glucocorticoids. Cell Research (2014) 24:713-726.

He, Y., et al. Discovery of a highly potent glucocorticoid for asthma treatment. Cell Discovery (2015) 1, 15035; doi:10.1038/celldisc.2015.35.

Hintermann, Samuel, et al. Identification of a series of highly potent activators of the Nurr1 signaling pathway. Bioorganic & Medicinal Chemistry Letters 17 (2007) 193-196.

Holgate, S.T., et al. The mechanisms, diagnosis, and management of severe asthma in adults. Lancet 2006; 368:780-793.

Kelly, H. W. Comparative potency and clinical efficacy of inhaled corticosteroids. College of Pharmacy and Department of Pediatrics, University of New Mexico Health Sciences Center, 5:4, pp. 537-553 Dec. 1999.

Lipworth, B.J. Systemic Adverse Effects of Inhaled Corticosteroid Therapy. A Systematic Review and Meta-analysis. Arch Intern Med. (1999); 159:941-955.

Onnis, V., et al. Rational structure-based drug design and optimization in the ligand-binding domain of the glucocorticoid receptor-α. Future medicinal chemistry 1.2 (2009): 345-359.

Rebeyrol, Carine, et al. Glucocorticoids reduce inflammation in cystic fibrosis bronchial epithelial cells. Cellular Signaling 24 (2012) 1093-1099.

Riether, D., et al. Nonsteroidal Dissociated Glucocorticoid Agonists Containing Azaindoles as Steroid A-Ring Mimetics. J. Med. Chem. 2010, 53, pp. 6681-6698.

(56) References Cited

OTHER PUBLICATIONS

Salter, M., et al. Pharmacological properties of the enhanced-affinity glucocorticoid fluticasone furoate in vitro and in an in vivo model of respiratory inflammatory disease. Am J Physiol Lung Cell Mol Physiol 293:L660-L667, (2007).

Schacke, H., et al. Dissociation of transactivation from transrepression by a selective glucocorticoid receptor agonist leads to separation of therapeutic effects from side effects. Proc Nat'l Aced Sci USA, Jan 6, 2004;101(1):227-232, copy not provided.

Sengupta, S., et al. "Alternate glucocorticoid receptor ligand binding structures influence outcomes in an in vivo tissue regeneration model." Comparative Biochemistry and Physiology Part C: Toxicology & Pharmacology 156.2 (Aug. 2012): pp. 121-129.

Shah, N., et al. Design and evaluation of novel nonsteroidal dissociating glucocorticoid receptor ligands. Bioorganic & Medicinal Chemistry Letters 14 (2004) pp. 5199-5203.

Stahn, C., et al. Molecular mechanisms of glucocorticoid action and selective glucocorticoid receptor agonists. Molecular and Cellular Endocrinology 275 (2007) pp. 71-78.

Syed, Y.Y. Fluticasone furoate/vilanterol: a review of its use in patients with asthma. Drugs (2015) 75:407-418.

Tamm, M., et al. Inhaled corticosteroid and long-acting β2-agonist pharmacological profiles: effective asthma therapy in practice. Respiratory Medicine (2012) 106(S1), S9-S19.

Tait, A.S., et al. The role of glucocorticoids and progestins in inflammatory, autoimmune, and infectious disease. Journal of Leukocyte Biology vol. 84, Oct. 2008 pp. 924-931.

Valotis, A., et al. Human receptor kinetics and lung tissue retention of the enhanced-affinity glucocorticoid fluticasone furoate. Respir Res 8:54 (Jul. 27, 2007).

Vayssiere, B.M., et al. Synthetic Glucocorticoids that Dissociate Transactivation and AP-1 Transrepression Exhibit Antiinflammatory Activity in Vivo. Molecular Endocrinology 1997, vol. 11, No. 9, pp. 1245-1255.

Vestbo, Jorgen, et al. Effectiveness of Fluticasone Furoate-Vilanterol for COPD in Clinical Practice. The New England Journal of Medicine 375;13 Sep. 29, 2016 pp. 1253-1260.

Villa, E., et al. A review of the use of fluticasone furoate since its launch. Expert Opinion on Pharmacotherapy 12(13):2107-2117 (2011).

Vippagunta, S.R., et al. Crystalline solids. Advanced Drug Delivery Reviews 48 (2001) 3-26.

Yongmei, X., et al. P082 Interleukin (IL)-6 deficiency does not affect motor neuron disease caused by superoxide dismutase 1 mutation. Abstract/Cytokine 59 (2012) 545.

PCT/US10/020901 International Search Report and Written Opinion dated Mar. 18, 2010.

PCT/US14/57497 International Search Report and Written Opinion dated Dec. 11, 2014.

* cited by examiner

Cortisol-bound GR LBD

MF-bound GR LBD

▓ DEX-Bound GR LBD
▓ MF-bound GR LBD

Cortisol          MF

Cortisol          DEX

MF

DEX

17α Furoate

MF

▓ DEX-bound GR LBD
▓ MF-bound GR LBD

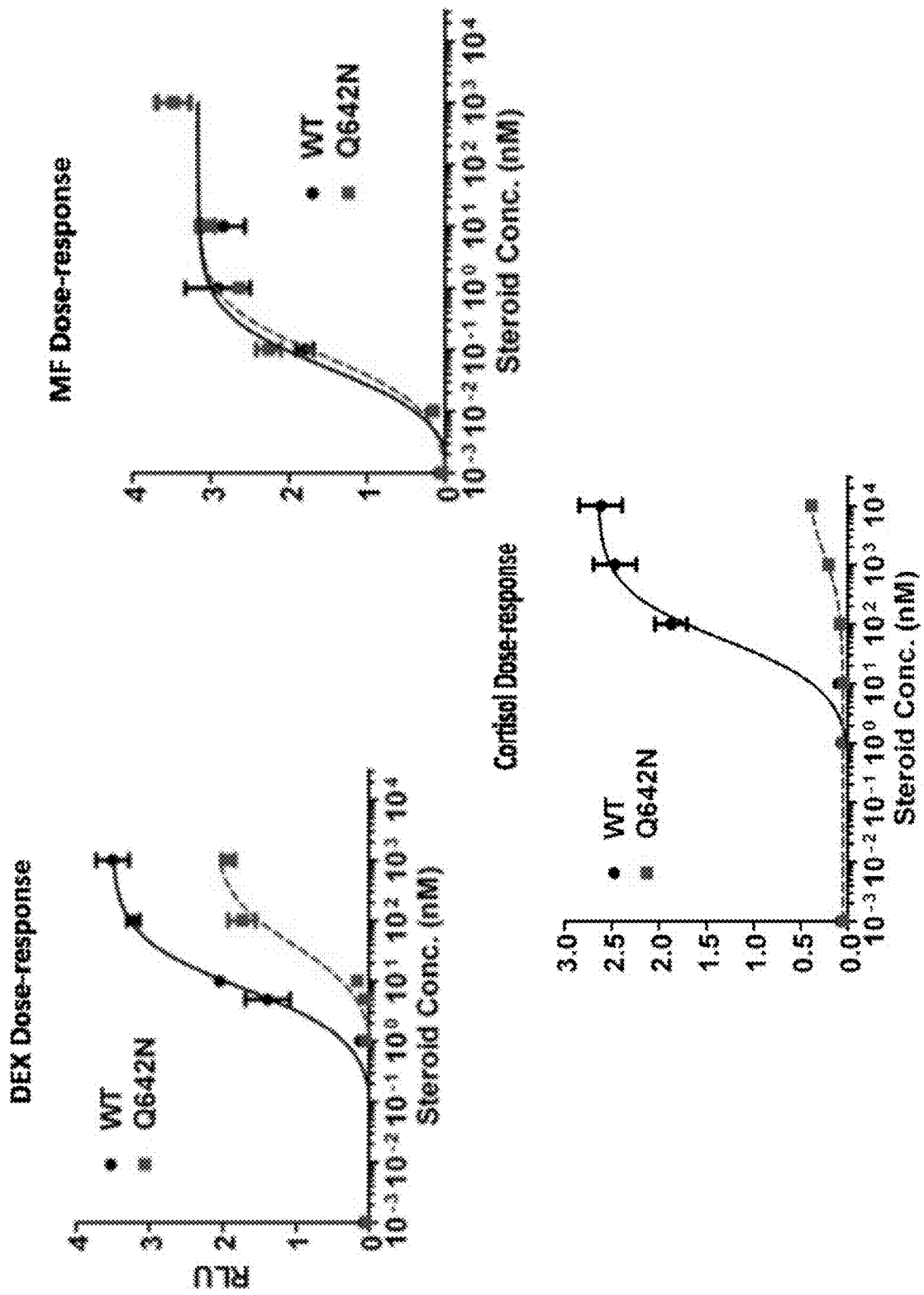

1: F602S
2: AYVTI
3: AYVTI EAEA
4: AYVTI KAKA

Cortisol-bound GR LBD

MF-bound GR LBD

DEX-bound GR LBD

Cortisol-bound GR LBD

DEX-bound GR LBD

Cortisol-bound GR LBD

*In vitro Reporter Assay*

*In vivo Animal Model*

STRUCTURES AND MECHANISM FOR THE DESIGN OF HIGHLY POTENT GLUCOCORTICOIDS

CROSS-REFERENCE TO RELATED APPLICATION

This application is a 35 USC § 371 United States national phase application of, and claims priority to, PCT International Application No. PCT/US2017/056447 filed Oct. 13, 2017, which claims priority to U.S. Provisional Application Ser. No. 62/408,314, filed Oct. 14, 2016. The entire contents of the aforementioned applications are incorporated herein by reference in their entirety.

FEDERAL FUNDING

This invention was made with government support under DK066202 and DK071662 awarded by the National Institute of Diabetes and Digestive and Kidney Diseases/National Institutes of Health. The government has certain rights in the invention.

TECHNICAL FIELD OF THE INVENTION

The present invention relates to novel glucocorticoid compounds. The invention also relates to methods of using these compounds, the synthesis of these compounds, and to compositions and formulations comprising the glucocorticoid compounds, and uses thereof.

BACKGROUND OF THE INVENTION

Glucocorticoids such as prednisone, dexamethasone (DEX), and budesonide are highly effective anti-inflammatory drugs. They are widely used to treat inflammation and autoimmune diseases such as asthma, arthritis, lupus, and Crohn's disease (1, 2). These drugs exert their physiologic roles through binding to the glucocorticoid receptor (GR), a ligand-activated transcriptional factor of the nuclear receptor superfamily. In the absence of glucocorticoid, GR resides in the cytoplasm and associates with chaperone proteins such as hsp90 and hsp70. The binding of hormone causes a conformational change in GR, leading to its translocation to the nucleus, where it exerts its transcriptional control activity, either activation (transactivation) or repression (transrepression). In transactivation, GR dimerizes, binds directly to a specific glucocorticoid response element, and then recruits coactivators to activate transcription. In transrepression, the general model is that GR binds other transcription factors (e.g., NF-κB, AP-1) to become indirectly tethered to their binding sites through protein-protein interactions. Upon being tethered near a target promoter, GR represses downstream gene expression (3). It is generally believed that transrepression does not require GR dimerization (4, 5).

Transrepression is the major mechanism through which glucocorticoids act as anti-inflammatory agents (6). The tethering of GR to the NF-κB/AP-1 promoter leads to the transcriptional repression of major downstream proinflammatory factors, including proinflammatory cytokines (e.g., TNF-α, IL-1β, and IL-6), chemokines (e.g., CCL2, CCL19), and enzymes associated with the onset of inflammation (e.g., COX2, MMP13, and phospholipase A2) (2). Because of their fast action and sustainable effect, glucocorticoids remain the first choice for treating inflammatory diseases. However, the long-term use of glucocorticoids, especially at high doses, has many adverse consequences, including diabetes mellitus/glucose intolerance, hypertension, obesity, and osteoporosis (7, 8). Most of these consequences are attributed to the transactivation of GR. For instance, glucocorticoids induce the genes encoding rate-limiting enzymes of the gluconeogenesis pathway in liver, glucose-6-phosphatase and phosphoenol pyruvate carboxykinase (9, 10), thus augmenting the de novo synthesis of glucose and eventually leading to weight gain or diabetes. Glucocorticoids also induce a key regulatory gene of bone development, Dickkopf-1 (DKK1), up-regulation of which leads to osteoporosis and bone loss (11). It is generally observed that many of the side effects of glucocorticoids are associated with high dose usage of glucocorticoids (12-14). For example, a "threshold pattern" was observed for the use of prednisone: at 7.5 mg per day, it causes glaucoma, depression and high blood pressure (12). These side effects are caused by GR transactivation as well as by non-target activation of other receptors such as mineralocorticoid receptor (MR), which activation cause high blood pressure (15). Thus, it is important to develop highly potent and selective glucocorticoids to reduce the unwanted side effects.

Potency and efficacy are two key pharmacokinetic parameters of glucocorticoids. While efficacy is the maximal activity a given drug can achieve, usually at maximal concentration, potency is the concentration of a given drug required to reach half maximal activity (EC50). For two glucocorticoids that have the same efficacy, a highly potent one will require a lower dose to achieve the same treatment effect (14, 15). Importantly, a glucocorticoid may have different potencies for transactivation and transrepression; for example, gene induction by GR via DEX requires a 5- to 6-fold higher glucocorticoid concentration than gene repression (16-18). This differential response provides an opportunity to develop highly potent glucocorticoids that can be used at low doses to achieve full repression of inflammation signals while with minimal transactivation activity and side effects. Finally, the development of insensitivity and resistance to glucocorticoid therapy is a major problem in treating common inflammatory diseases such as chronic obstructive pulmonary disease, rheumatoid arthritis and inflammatory bowel disease (19). Glucocorticoid resistance is also an unsolved issue for white blood cell cancers, especially childhood acute leukemia (20). Several mechanisms of glucocorticoid resistance have been identified or proposed, including a change of kinase pathways, alteration of cofactors, and loss or mutation of receptors (19, 21). One common observation is that the affinity of ligand for receptor is decreased in glucocorticoid-resistant patients. Such patients treated with highly potent glucocorticoids have shown improvement, but the effect gradually decreased (22). Therefore, there is an urgent need to develop a new generation of more potent glucocorticoids.

Cortisol is an endogenous glucocorticoid produced by the adrenal gland. Cortisol has low potency and receptor binding ability relative to the most commonly used synthetic glucocorticoid, such as DEX (23). On the other side, Mometasone Furoate (MF) is a potent glucocorticoid used to treat inflammatory skin disorder (Elocon), asthma (Asmanex), and nasal sinus inflammation (Nasonex) (24, 25). MF has a lipophilic furoate ester at the C17α position of steroid D ring, which is believed to be the origin of its high potency (26). Here the inventors determined the crystal structures of the GR LBD bound to MF and cortisol, which reveal the underlying mechanism that discriminates the ligand potency between MF and cortisol. We then used the observed structure mechanism to design several novel glucocorticoids with much improved potency and efficacy, which could serve as the starting leads for therapeutic development for treating inflammatory diseases.

SUMMARY OF THE INVENTION

The evolution of glucocorticoids drugs was driven by the demand of lowering the unwanted side effects, while keeping the beneficial anti-inflammatory effects. Potency is a very important aspect of this evolution as many undesirable side effects are associated with high doses. The side effects can be minimized by highly potent glucocorticoids that achieve the same treatment effects at lower doses. This demand propelled the evolution of glucocorticoids from low to high potency. Cortisol is an endogenous glucocorticoid which has a relatively low potency while Mometasone Furoate (MF) is a highly potent synthetic glucocorticoid that has been used in treating many inflammation diseases. To understand the underlying mechanisms that drove the evolution of glucocorticoids, the inventors determined the X-ray structures of the glucocorticoid receptor (GR) ligand binding domain (LBD) bound to cortisol and MF. The cortisol-bound GR LBD revealed that the flexibility of the 1,2 single bond in the steroid A ring is primarily responsible for the low affinity of cortisol to GR. Meanwhile, the MF-bound GR LBD unveiled that the high potency of MF is achieved by its 17a furoate group, which completely fills the ligand binding pocket, thus providing additional anchor contacts for high affinity binding. A single amino acid in the ligand binding pocket, Q642, plays a discriminating role in ligand potency between MF and cortisol. Structure-based design led to synthesis of several novel glucocorticoids with much improved potency. Together these results reveal key structural mechanisms of glucocorticoid potency and provide a rational basis for developing highly potent glucocorticoids.

In one aspect, the invention provides a compound of Formula I

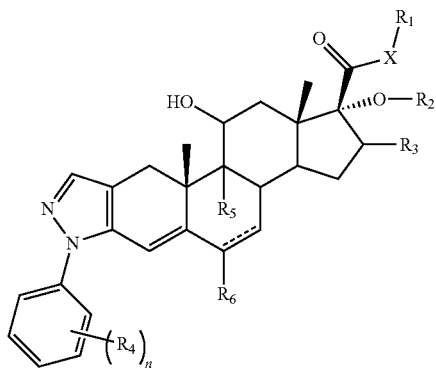

or a pharmaceutically acceptable salt thereof, wherein X is —O— or —S—; ----- is a bond or is absent; $R_1$ is selected from hydrogen, $C_{1-6}$ alkyl, cycloalkyl, aryl, heteroaryl, aralkyl, heteroaralkyl, or heterocycloalkyl, any of which is optionally substituted; $R_2$ is -L-R'— wherein L is a bond or —C(O)— and R' is selected from hydrogen, $C_{1-6}$ alkyl, cycloalkyl, aryl, heteroaryl, aralkyl, heteroaralkyl, or heterocycloalkyl, wherein R' is optionally substituted; $R_3$ is hydrogen or optionally substituted $C_{1-6}$ alkyl; each $R_4$ is independently $C_{1-6}$ alkyl, —OH, halo, haloalkyl, —CN, —NO$_2$, —C(O)($C_{1-6}$ alkyl), —NHC(O)($C_{1-6}$ alkyl), —OC (O)($C_{1-6}$ alkyl), —C(O)NH($C_{1-6}$ alkyl), —C(O)O($C_{1-6}$ alkyl), —SO$_2$($C_{1-6}$ alkyl), or —SO$_2$NH($C_{1-6}$ alkyl), wherein the alkyl of $R_4$ is optionally substituted; each of $R_5$ and $R_6$ is independently selected from hydrogen, halo, or $C_{1-4}$ alkyl; and n is 0, 1, 2, 3, 4, or 5.

DETAILED DESCRIPTION OF THE FIGURES

Figure 1B:
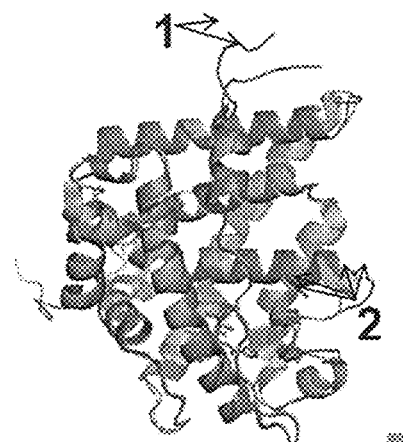
Figure 1B:
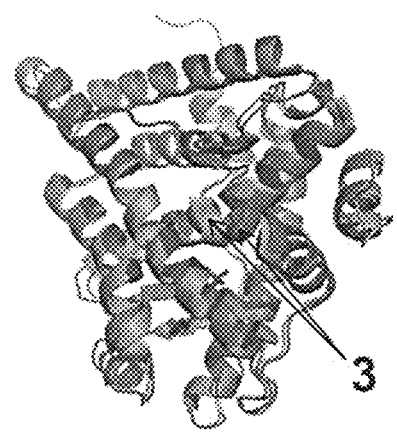
Figure 1C:
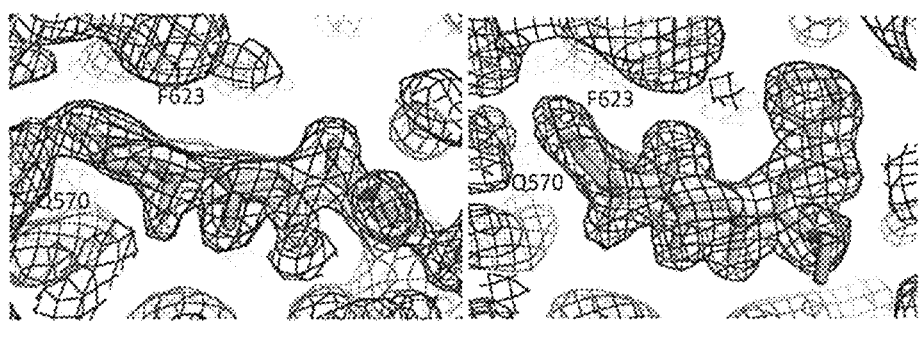

FIGS. 1A-1C: Overall structure of cortisol-bound GR LBD and MF-bound GR LBD. (FIG. 1A) Architecture of Cortisol-bound GR LBD and MF-bound GR LBD. (FIG. 1B) Structural comparison of the DEX-bound GR LBD and the MF-bound GR-LBD. Arrows indicate differences between the two, 1: loop region before helix 1; 2: loop region before helix 5 to helix 7; 3: orientation of The C-terminal of the AF2 helix. (FIG. 1C) Electron density map of cortisol and MF in the ligand binding pocket of GR LBD.

FIGS. 2A-2D: Potency of cortisol, DEX and MF. (FIG. 2A) Chemical structures of cortisol, DEX, and MF. Steroid rings (FIGS. 2A-2D) are indicated. Key atom numerations marked as small scripts near the right positions. The difference between DEX and cortisol is indicated in DEX structure. The furoate group of MF is indicated. (FIGS. 2B-2C) Dose-response curves for cortisol, DEX and MF for the induction reporter MMTV-Luc and the repression reporter AP1-Luc in AD293 cells, RLU: Relative Luciferase Unit. Error bars stand for standard deviation, n=3. (FIG. 2D) In vitro GR binding assay for MF, DEX, and cortisol. CPM: count per second. Error bars stand for standard deviation, n=2.

Figure 3A:
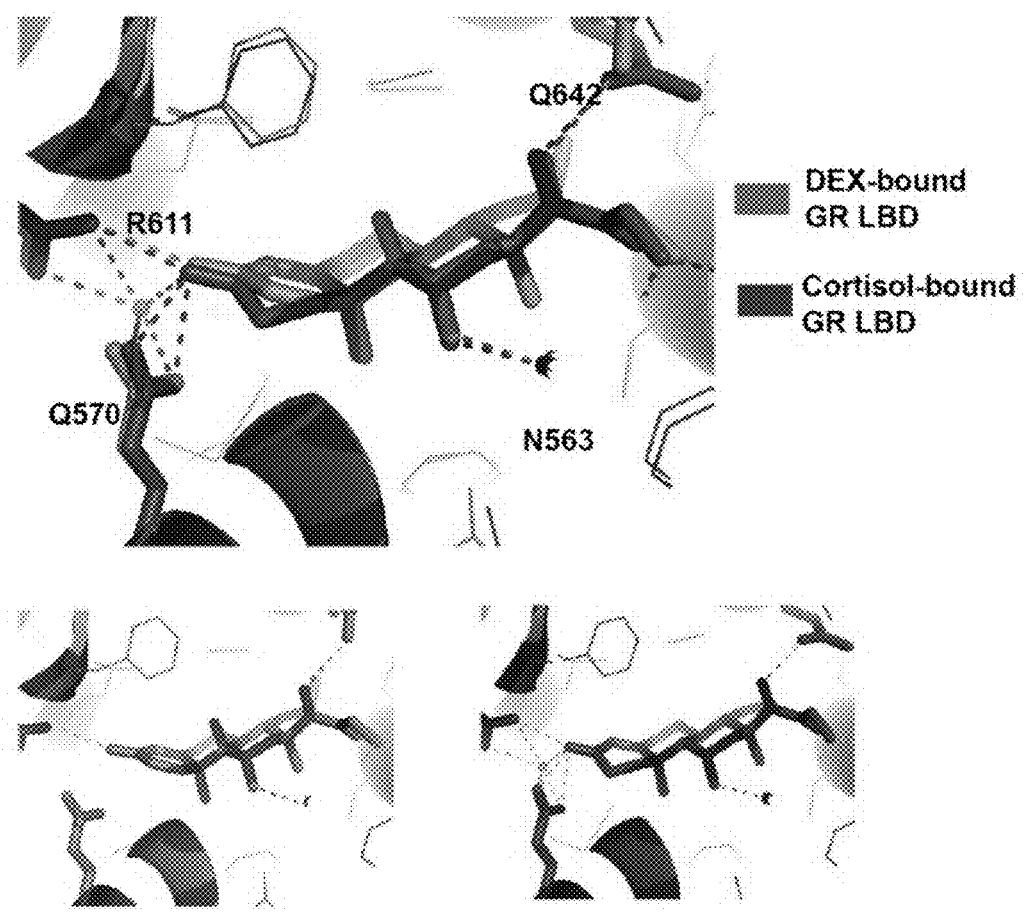
Figure 3B:
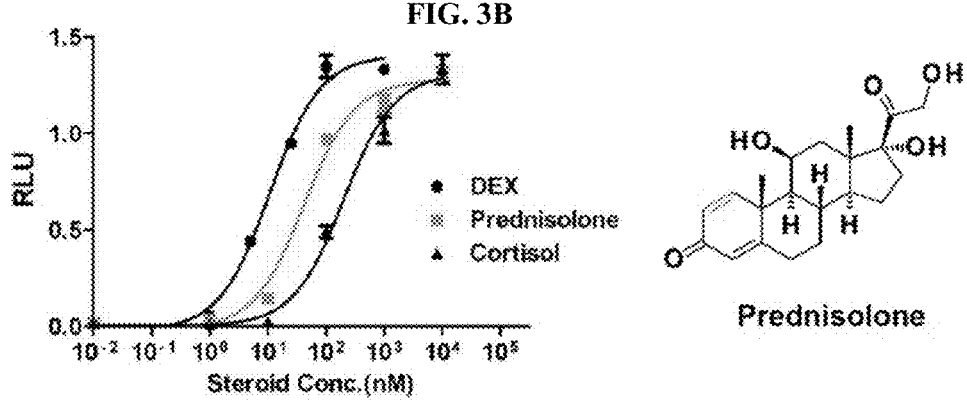

FIGS. 3A-3B: The flexibility of 1,2 single bond attributes to the low affinity of cortisol. (FIG. 3A) Hydrogen bond network of cortisol and DEX in the ligand binding pocket of GR LBD. (FIG. 3B) Dose response curves of cortisol, prednisolone and DEX for GR transactivation on MMTV-Luc in AD293 cells. Prednisolone differentiates from cortisol only by 1,2 double bond. Error bars stand for standard deviation, n=3.

FIGS. 4A-4D: The full occupancy of 17α furoate group in GR ligand binding pocket. (FIGS. 4A, 4B) Three-dimensional structures of DEX and MF. (FIG. 4C) Alignment of DEX and MF in the ligand binding pocket of GR LBD. The 17α furoate group of MF expands the GR ligand binding pocket and fully occupies the hydrophobic cavity above the steroid D ring. (FIG. 4D) Detailed hydrophobic interactions of the 17α furoate group with residues in the hydrophobic cavity of GR LBD ligand binding pocket.

Figure 5A:
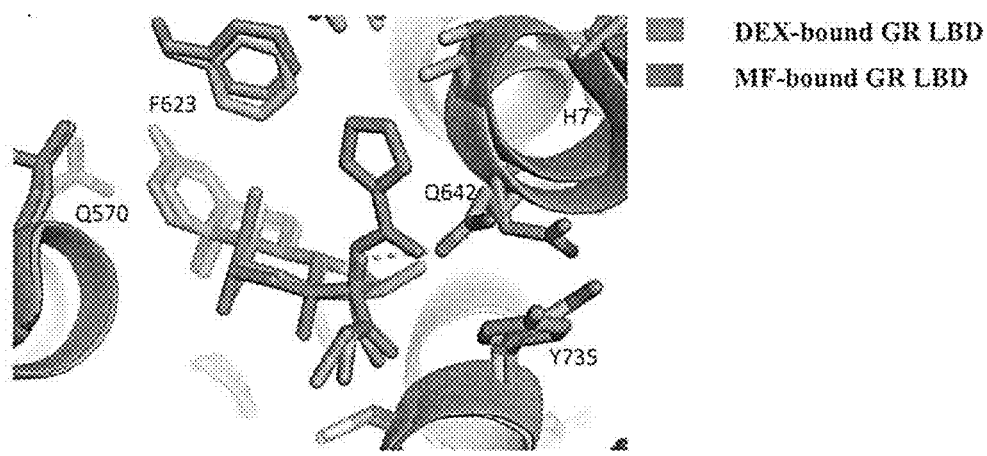
Figure 5B:
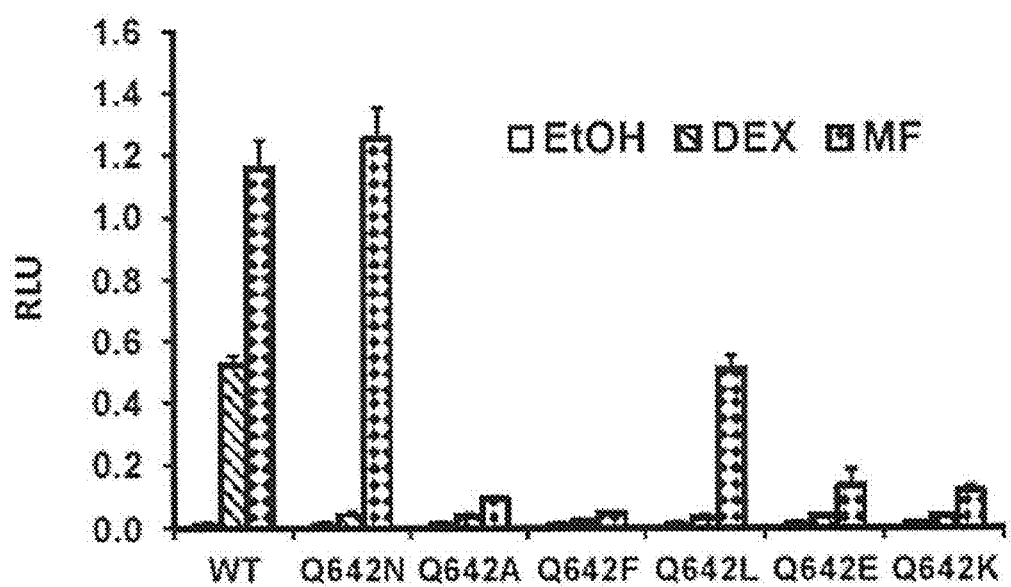

FIG. 5A-5C: Q642 plays critical roles in recognizing ligand of different potency. (FIG. 5A) Detailed interaction of Q642 with different ligands: DEX-bound GR-LBD, and MF-bound GR-LBD. (FIG. 5B) Transactivation activity of Q642 mutations at an unsaturated concentration of steroid (DEX 10 nM; MF 1 nM). Error bars stand for standard deviation, n≥3. (FIG. 5C) Dose-response curves for MF, DEX, and cortisol of wild type (WT) GR and the Q642N mutant on MMTV-Luc in AD293 cells. Error bars stand for standard deviation, n=3.

Figure 6:
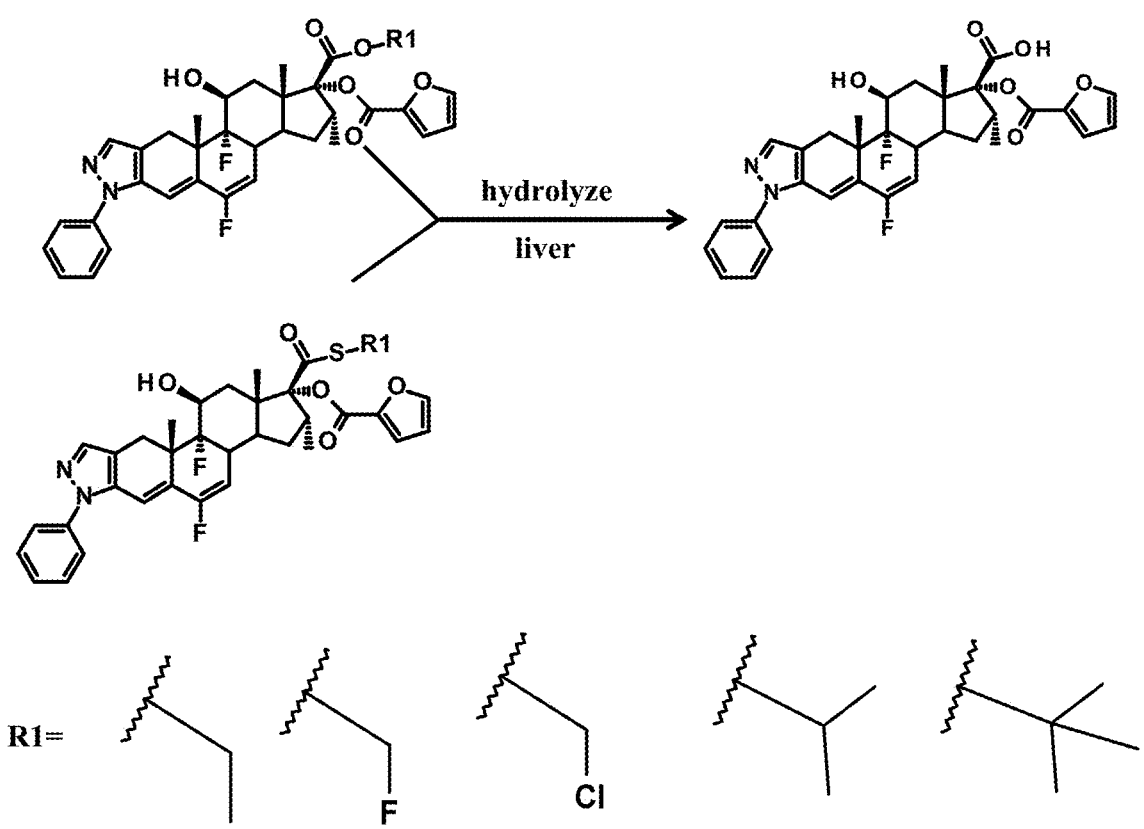
Figure 6:
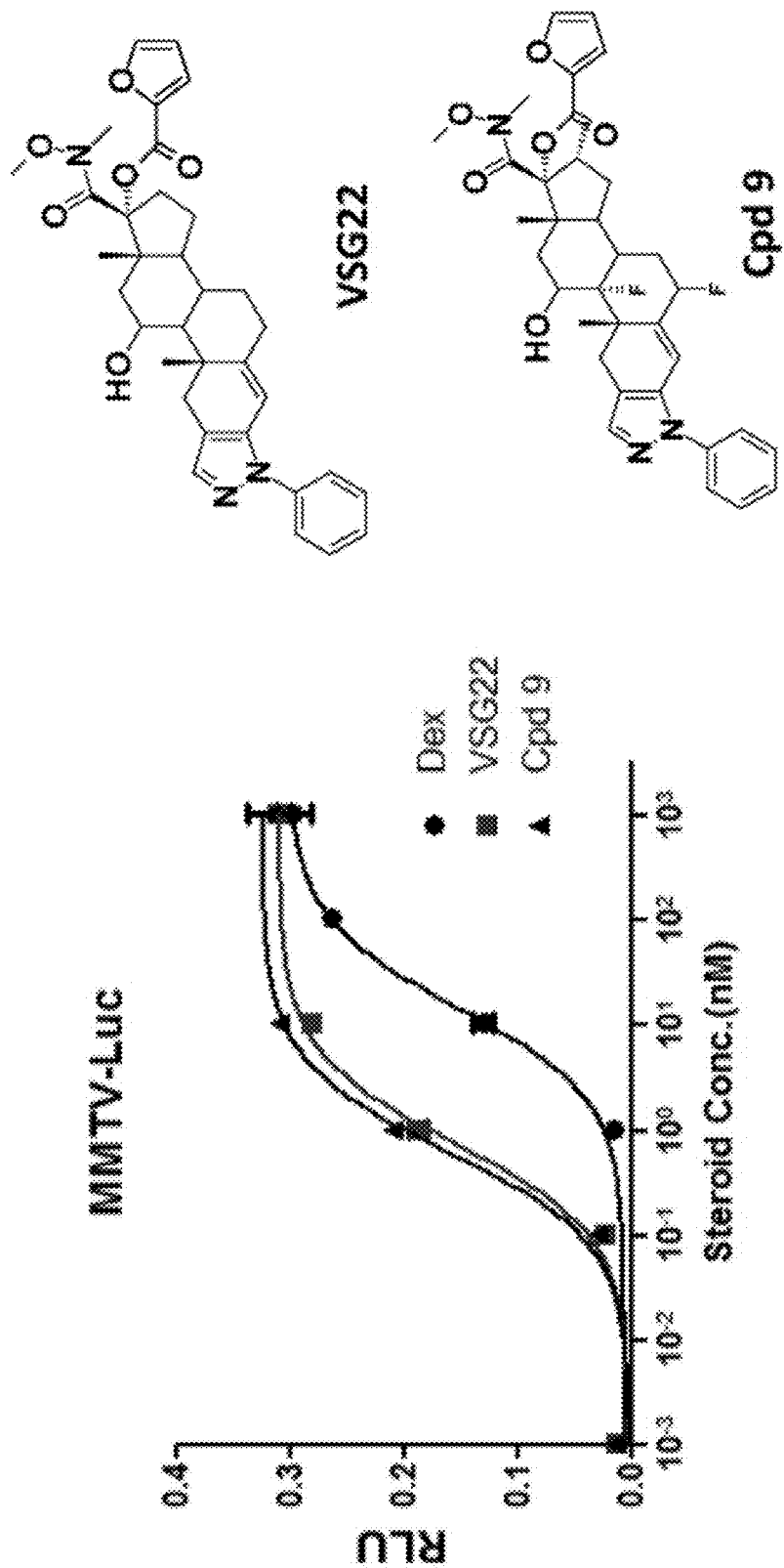

FIG. 6: Design of —O— or —S— ester compounds, and subsequent liver hydrolysis.

Figure 7:
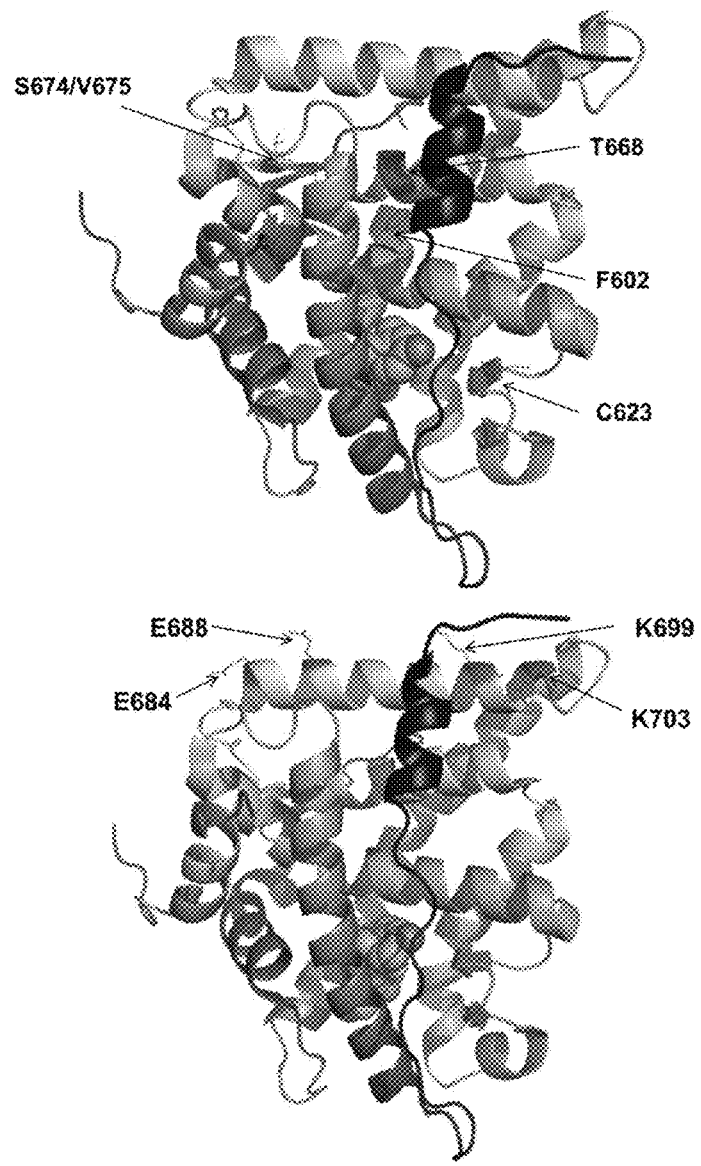

FIG. 7: Positions of solubility mutations and crystallization mutations". Upper panel: positions of mutations that solubilize GR LBD; lower panel: surface mutations that facilitate crystallization of GR LBD.

Figure 8:
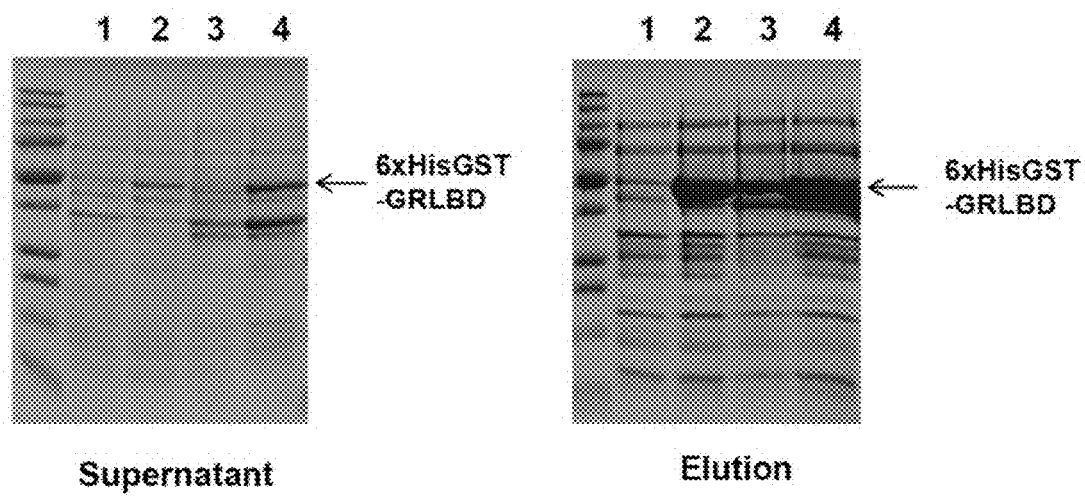

FIG. 8: Protein expression and purification of selected GR LBD mutations. GR LBD mutants were expressed and purified in the presence of 10 μM cortisol.

Figure 9A:
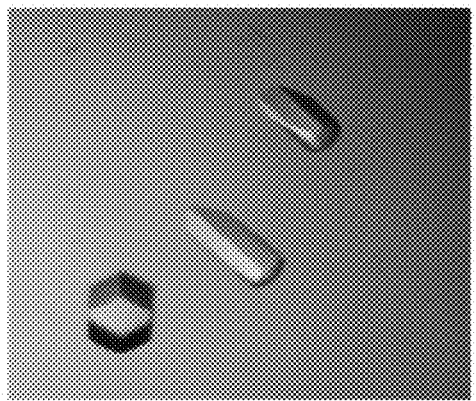
Figure 9A:
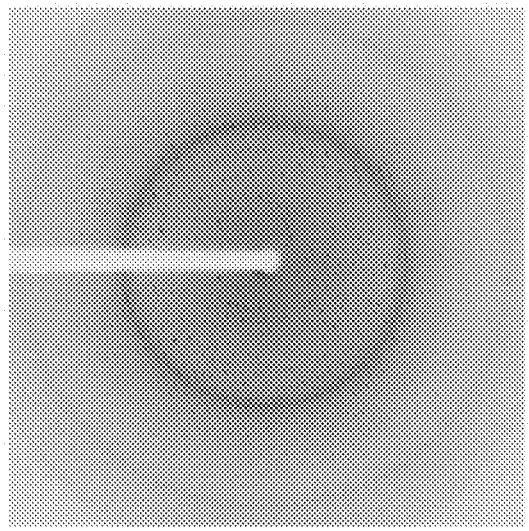
Figure 9B:
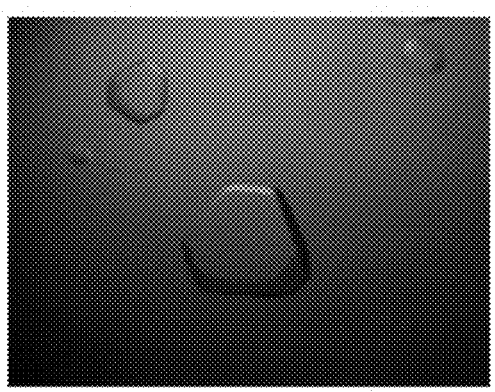
Figure 9B:
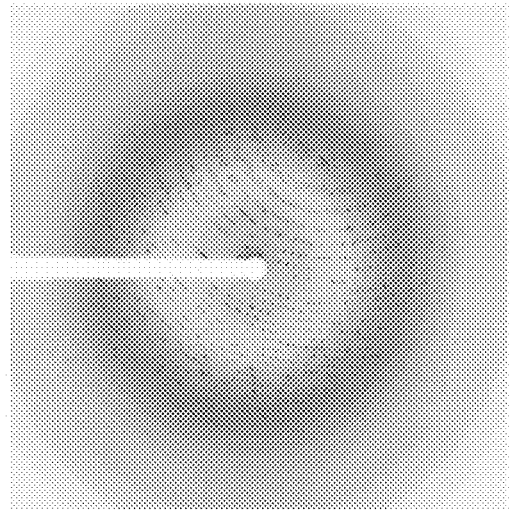

FIG. 9A-9B: Protein crystals and diffraction maps of cortisol- and MF-bound GR LBD. (FIG. 9A) Cortisol-bound GR LBD. (FIG. 9B) MF-bound GR LBD.

Figure 10A:
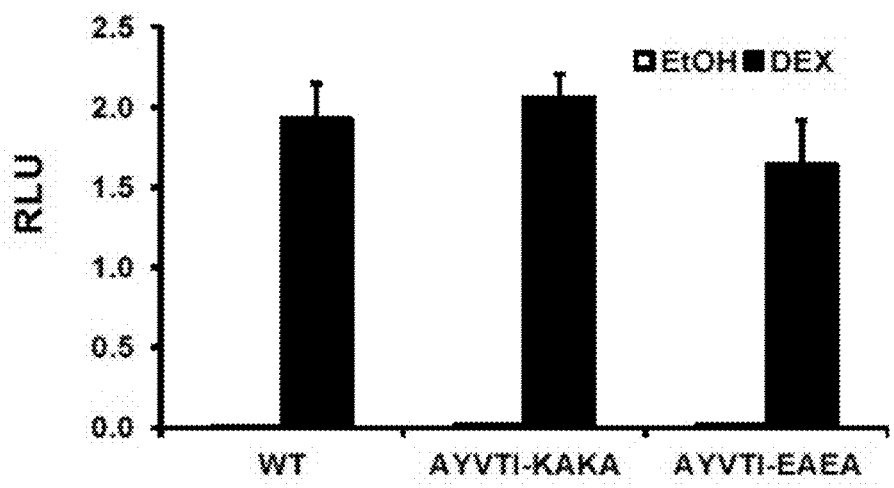
Figure 10B:
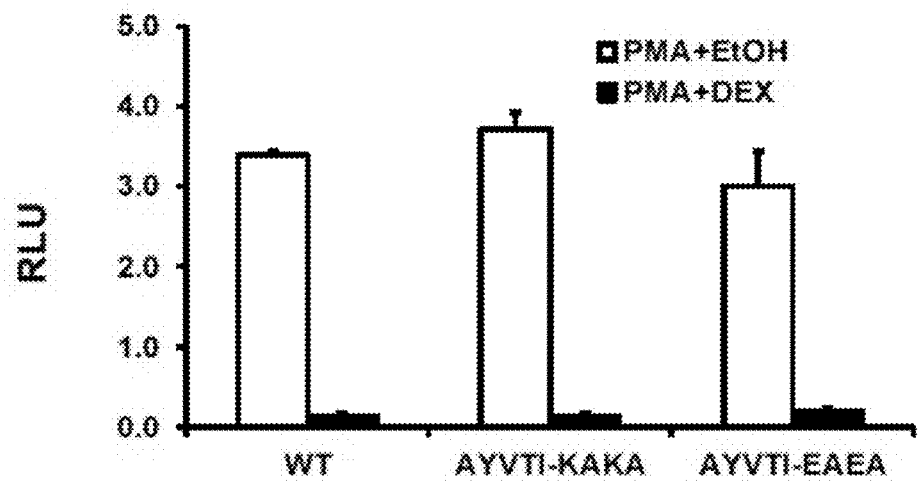

FIG. 10A-10B: The transcriptional activities of GR AYVTI mutations. (FIG. 10A) Transactivation activity of GR AYVTI mutations on MMTV-Luc in AD293 cells. DEX, 100 nM. Error bars stand for standard deviation, n=3. (FIG. 10B) Transrepression activity of GR AYVTI mutations on AP1-Luc in AD293 cells. DEX, 100 nM. Error bars stand for standard deviation, n=3.

Figure 11A:
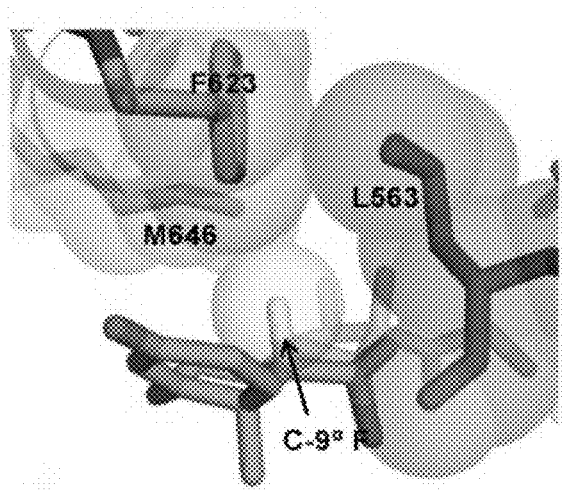
Figure 11A:
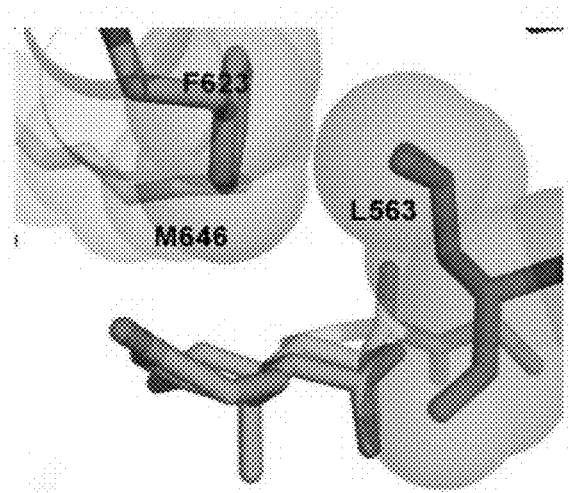
Figure 11B:
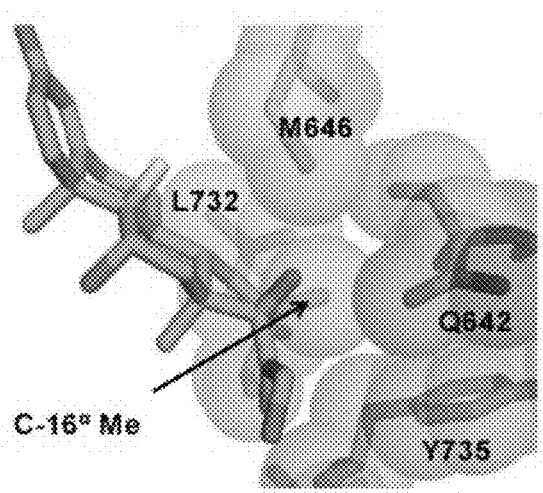
Figure 11B:
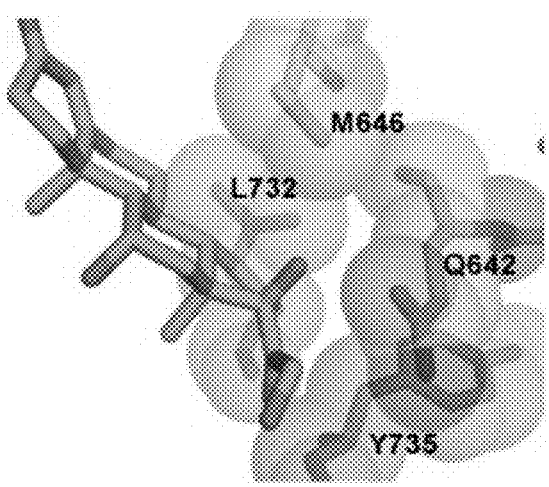

FIG. 11A-11B: Detailed structural comparisons of the steroid C-9α group and C-16 group of DEX and cortisol in the ligand binding pocket of the GR LBD. (FIG. 11A) The F atom at the C-9α position of DEX makes a close contact with F623, L563 and M646 in the ligand binding pocket of GR LBD. (FIG. 11B) The C-16 methyl group of DEX makes close contacts with Y735, L732, M646 and Q642 in the ligand binding pocket of the GR LBD.

Figure 12A:
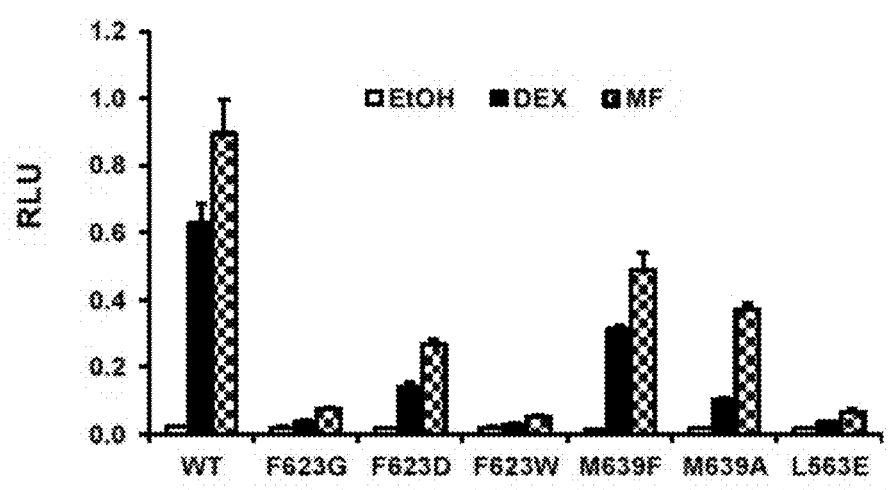
Figure 12B:
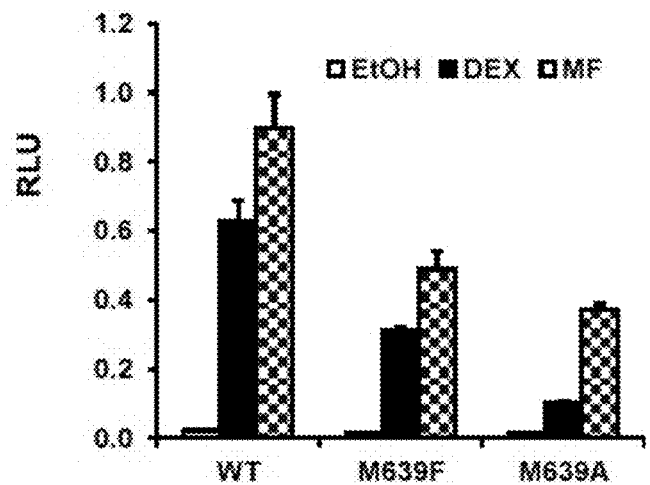

FIG. 12A-12B: The F623 and M639 mutations cannot separate activity of MF and DEX. (FIG. 12A) Transactivation activity of F623 mutations on MMTV-Luc in AD293 cells. DEX 10 nM, MF 1 nM. Error bars stand for standard deviation, n=3. (FIG. 12B) Transactivation activity of M639 mutations on MMTV-Luc in AD293 cells. DEX 10 nM, MF 1 nM. Error bars stand for standard deviation, n=3.

Figure 13A:
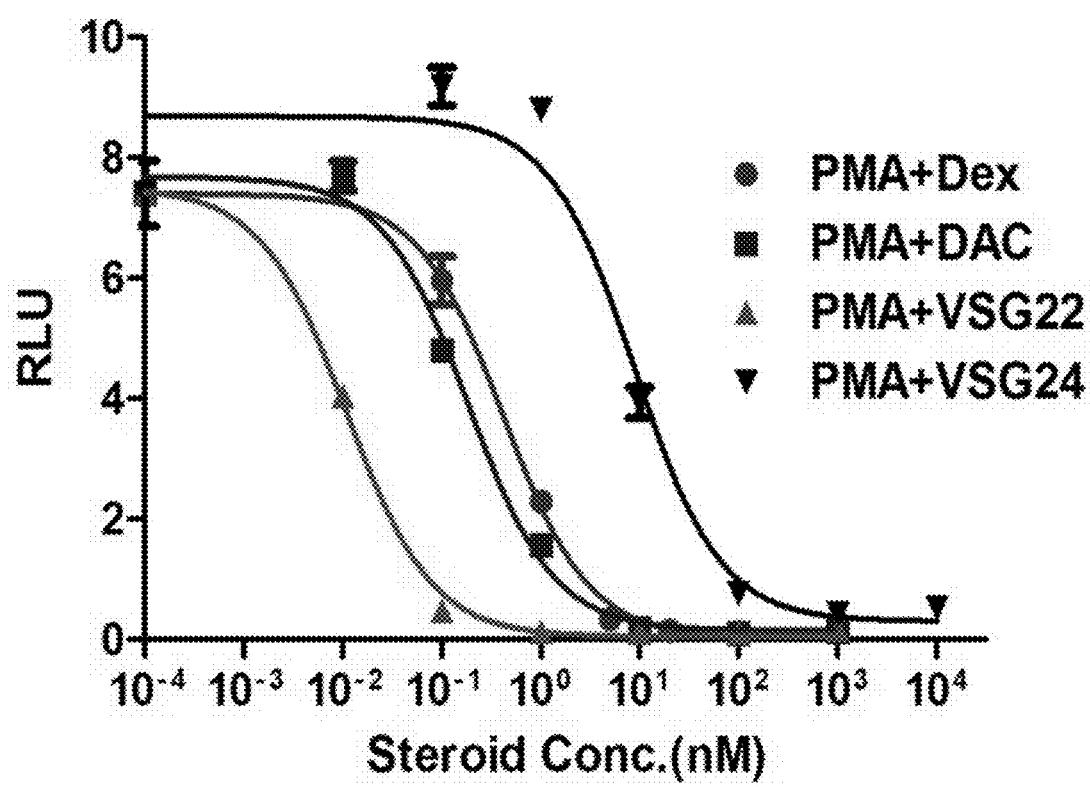
Figure 13B:
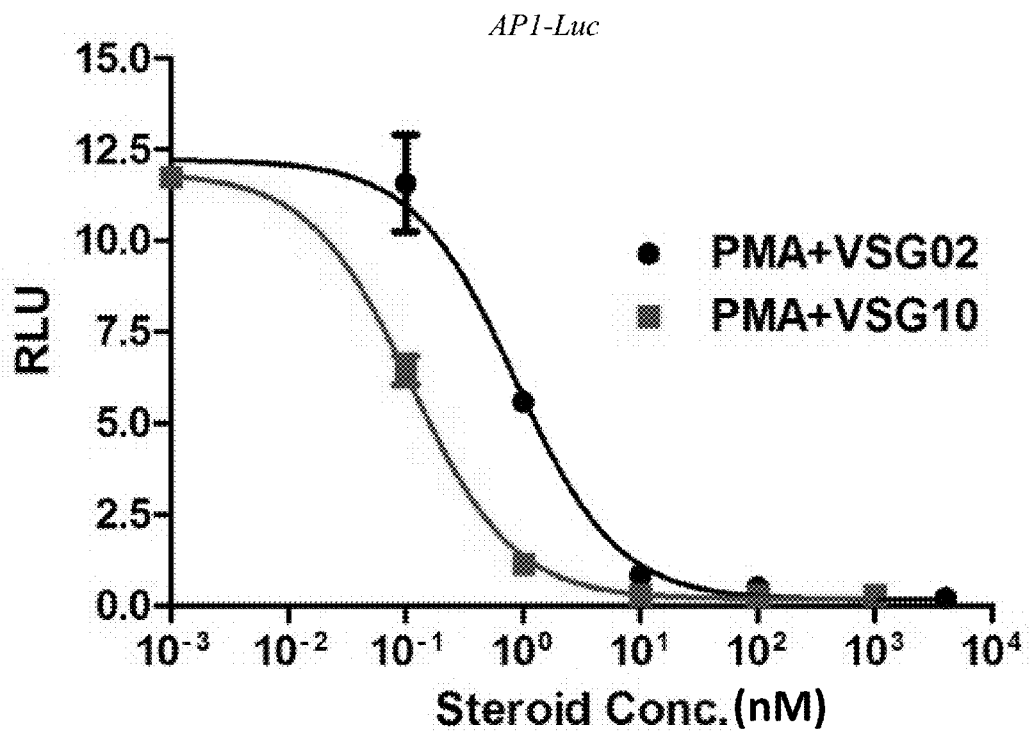
Figure 13B:
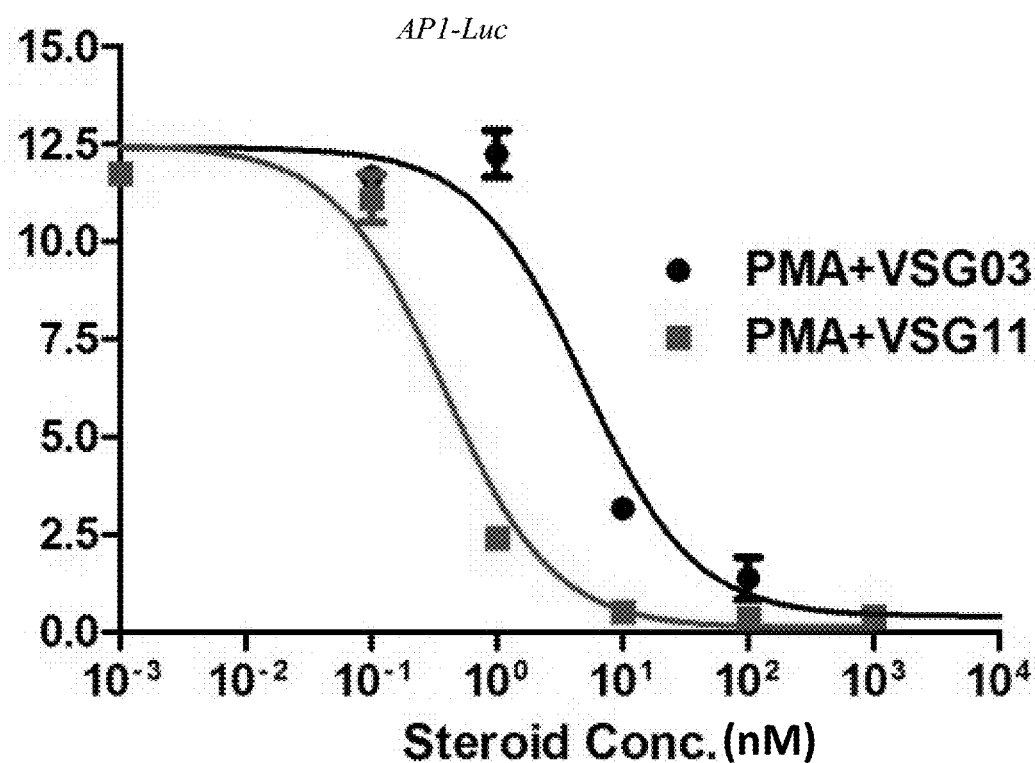
Figure 13B:
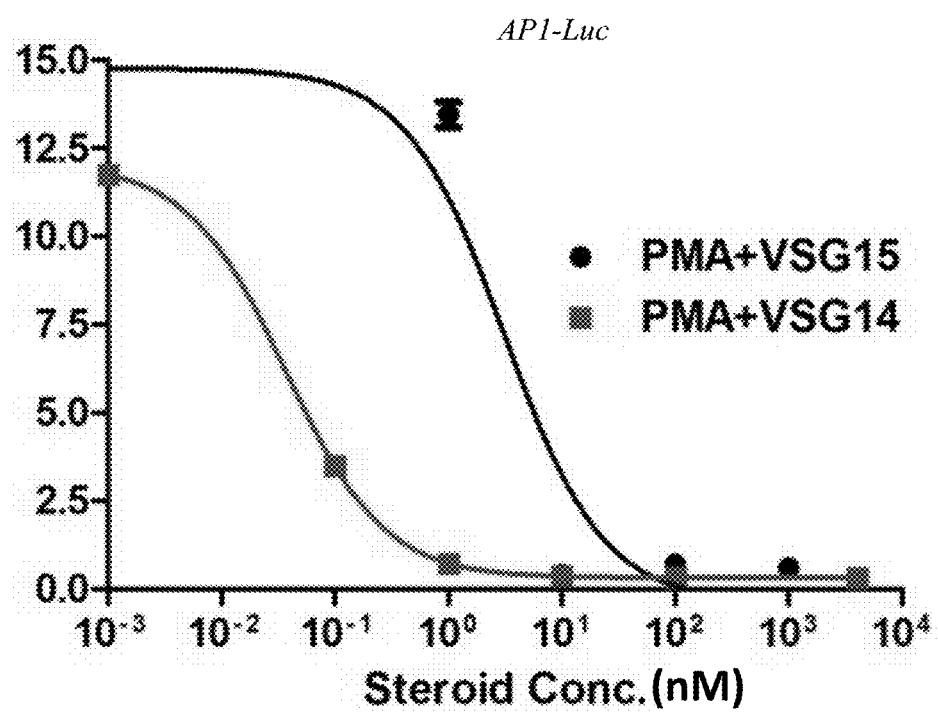

FIG. 13A-13B: In vitro binding assay of GR Q642A mutant protein. (FIG. 13A) in vitro ligand binding experiment using cytosol from AD293 cells that expressed either wild type GR or Q642A mutant GR. CPM: counts per minute. Error bars stand for standard deviation, n=2. (FIG. 13B) DEX dose response curve of WT GR and Q642A GR in a MMTV-Luc reporter assay. Error bars stand for standard deviation, n=3. (C), GR Q642A ligand competition assay. Error bars stand for standard deviation, n=2.

Figure 14:
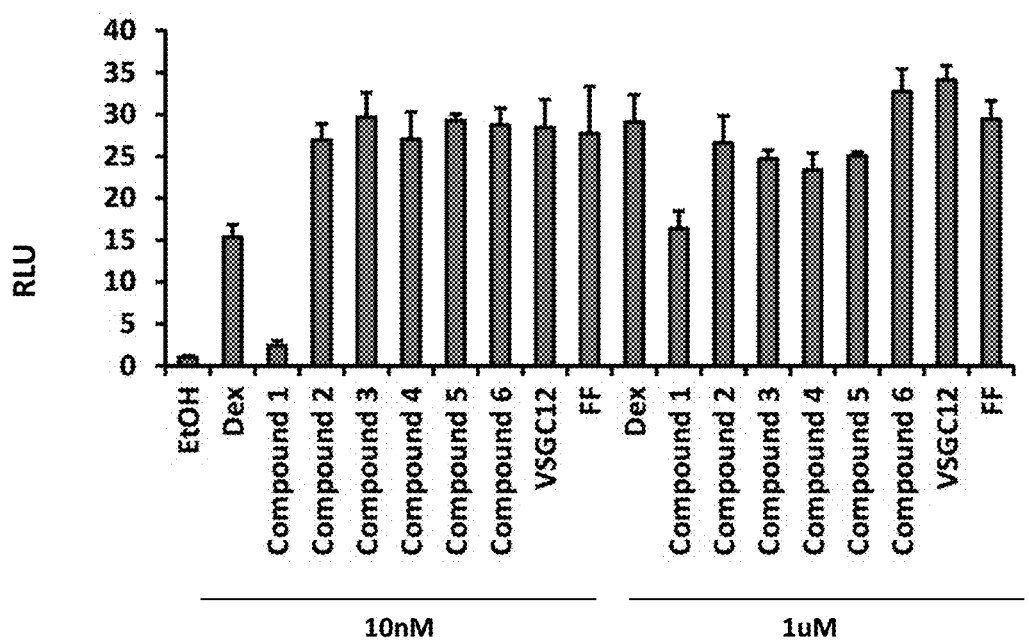

FIG. 14: Activity bar graph of the compounds of the invention, provided as Relative Luciferase Units.

Figure 15:
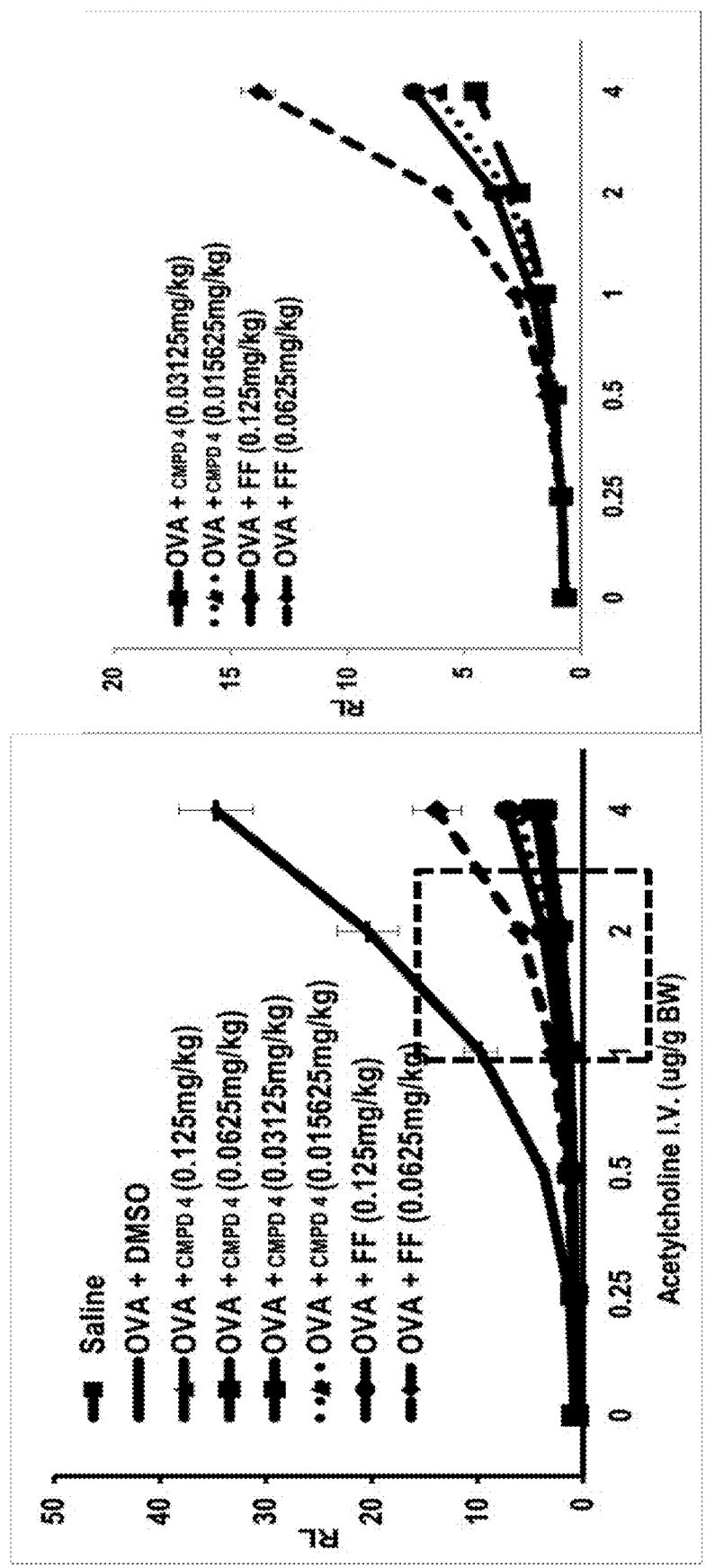

FIG. 15: Line graph showing the 8-fold increase in potency of Compound 4 over fluticasone furoate (FF).

Figure 16A:
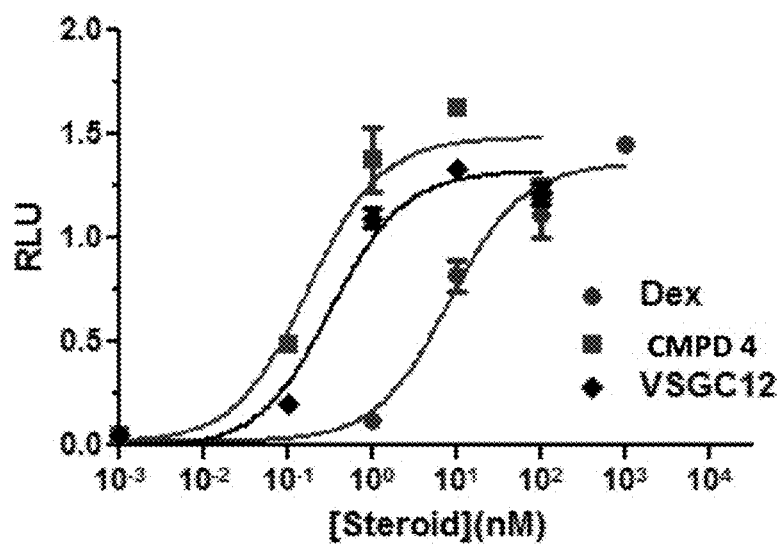
Figure 16B:
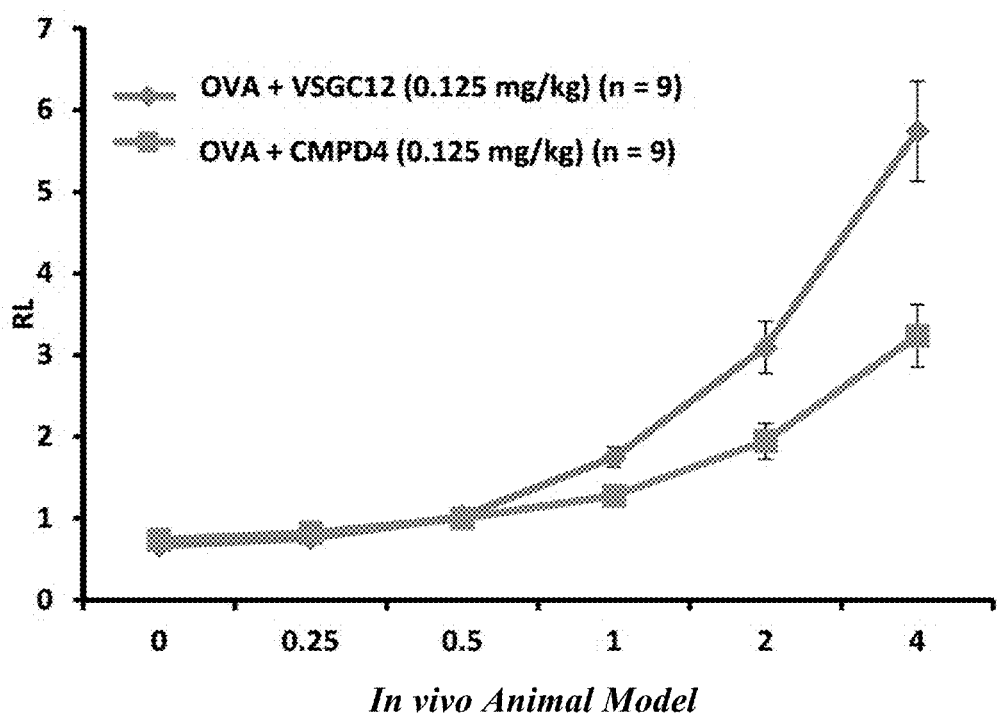

FIGS. 16A-16B: (FIG. 16A) A line graph providing the potency of candidate compounds in a reporter system. (FIG. 16B) A line graph providing the evaluation of the effect of candidate compounds in repressing lung inflammation, using a OVA-induced mouse asthma model.

The foregoing figures are provided for exemplary purposes, and are not meant to be limiting in any way.

DETAILED DESCRIPTION

Glucocorticoids have been in use for almost 60 years and they remain the first choice for treating many inflammatory and autoimmune diseases. However, long-term use of glucocorticoids can cause many adverse effects. Understanding the structural basis of GR activation and repression is very important for developing novel glucocorticoids with less side effects. However, the low expression level of GR in bacterial system, especially for low affinity ligand, hampered the structural study of this important cellular regulator. Via comparing conserved residues in steroid receptor family, the inventors had successfully identified amino acid mutations that could facilitate receptor expression without affecting receptor physiology function. This method will accelerate the structural study of GR, especially for those low affinity ligands, such as non-steroid ligand, which may hold the future of next generation glucocorticoid.

The development of highly potent glucocorticoids was propelled by two types of urgencies, one is the side effects of glucocorticoids caused by high dose usage, and the other is the clinical glucocorticoid resistant symptoms. While ligand affinity is a determining factor in potency, it is not the only one. Cellular cofactors also play crucial roles by recognizing surface differences caused by ligand binding, and subtle variations induced by binding of different ligands can have profound effects on cofactor selectivity. Different strategies had been applied to modify the rigid cortisol backbone to increase potency, and led to the development of DEX. A structural comparison of cortisol-bound GR LBD and DEX-bound GR LBD shows that among the modifications, the $\Delta^1$ double bond is critical for optimally positioning the C3 ketone, which forms a key hydrogen bond with R611. Subsequently, researchers found that a lipophilic ester group, such as an alkyl or propionate ester (26), at the C-17α position can strongly enhance glucocorticoid activity. One of the most commonly used asthma drugs, fluticasone propionate (FP), was generated by replacing the hydroxyl group with a propionate ester at the C-17α position. These data suggested the presence of a hydrophobic cavity above the steroid D ring in the ligand-binding pocket. Further optimization of FP with a furoate ester group to replace the propionate ester created a highly potent glucocorticoid, fluticasone furoate (FF), indicating that the furoate group might fit best in the cavity. Although the structure of the FF-bound GR LBD had been solved (35), the structural mechanism of the high potency of MF was not defined. Here, the inventors have discovered that the high potency of MF is attributable to both the C-17α furoate group occupying the full ligand-binding pocket and the surface conformation changes caused by ligand binding. Using mutagenesis, the inventors demonstrated that a single amino acid residue, Q642, plays a crucial role in recognizing the C-17α furoate group and coordinating the positioning of other amino acid side chains. Q642N differs from the wild-type protein by only one methyl group, yet is sufficient to completely separate the activities of MF, DEX, and cortisol, indicating how precisely the receptor activity is regulated.

The inventors have demonstrated that the C-17α furoate group can serve as an "anchor" point to position low-affinity ligands precisely and firmly in the ligand-binding pocket. The success in modifying DAC derivatives designed for increased dissociating properties demonstrates a robust strategy for designing therapeutic dissociated glucocorticoids, glucocorticoids with reduced clinical glucocorticoid resistance symptom, or non-steroid glucocorticoid compounds (those compounds generally show poor affinity to receptor). In summary, we have solved the first crystal structure of the GR LBD bound to a physiological ligand, the low-potency glucocorticoid cortisol, as well as the structure of the LBD bound to the clinically important high-potency synthetic ligand MF. In combination with biochemical and mutational analysis, the inventors have structurally identified the critical determinants of glucocorticoid affinity and potency, and validated these determinants through structure-based design and synthesis of highly potent glucocorticoids.

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.:

Smith, M. B. and March, J., John Wiley & Sons, New York: 2001, the entire contents of which are hereby incorporated by reference.

For the purposes of this invention, the carbon numbering for Compounds of Formula I is the accepted convention for steroid structures. Accordingly, compounds of Formula I are numbered as follows:

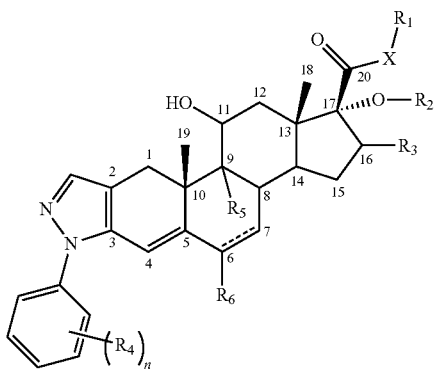

As described herein, compounds of the invention may optionally be substituted with one or more substituents, such as are illustrated generally above, or as exemplified by particular classes, subclasses, and species of the invention.

As described herein, "protecting group" refers to a moiety or functionality that is introduced into a molecule by chemical modification of a functional group in order to obtain chemoselectivity in a subsequent chemical reaction. Standard protecting groups are provided in Wuts and Greene: "Greene's Protective Groups in Organic Synthesis" 4th Ed, Wuts, P. G. M. and Greene, T. W., Wiley-Interscience, New York: 2006.

As used herein, the term "hydroxyl" or "hydroxy" refers to an —OH moiety.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, 1- or 2-isopropenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfanyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)—N(R$^X$)— or —N(R$^X$)—C(O)— when used internally, wherein R$^X$ and R$^Y$ can be hydrogen, aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—, where R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a C$_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a C$_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, bicyclo[2.2.2]octenyl, or bicyclo[3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic) carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) al iphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophene-yl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino) heteroaryl and ((dialkyl)amino)heteroaryl]; (amido) heteroaryl [e.g., aminocarbonylheteroaryl, ((alkylcarbonyl) amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy) heteroaryl; (sulfamoyl)heteroaryl [e.g., (aminosulfonyl)heteroaryl]; (sulfonyl)heteroaryl [e.g., (alkylsulfonypheteroaryl]; (hydroxyalkyl)heteroaryl; (alkoxyalkyl)heteroaryl; (hydroxy)heteroaryl; ((carboxy)alkyl)heteroaryl; (((dialkyl)amino)alkyl]heteroaryl; (heterocycloaliphatic)heteroaryl; (cycloaliphatic)heteroaryl; (nitroalkyl)heteroaryl; (((alkylsulfonyl)amino)alkyl) heteroaryl; ((alkylsulfonyl)alkyl)heteroaryl; (cyanoalkyl) heteroaryl; (acyl)heteroaryl [e.g., (alkylcarbonyl) heteroaryl]; (alkyl)heteroaryl; or (haloalkyl)heteroaryl [e.g., trihaloalkylheteroaryl].

A "heteroaraliphatic" (such as a heteroaralkyl group) as used herein, refers to an aliphatic group (e.g., a C$_{1-4}$ alkyl group) that is substituted with a heteroaryl group. "Aliphatic", "alkyl", and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tricyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbomanyl, bicyclo[3.2.1]octyl, bicyclo[2.2.2]octyl, bicyclo[3.3.1]nonyl, bicyclo[3.3.2]clecyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, aralkyl, aralphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the groups —CF$_3$, —CHF$_2$, and —CH$_2$F.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic (amido(aliphatic)))-S(O)$_2$— or the like.

As used herein, a "sulfoxy" group refers to —O—S(O)—R$^X$ or —S(O)—O—R$^X$, when used terminally and —OS(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$ when used internally, wherein R$^X$, R$^Y$, and R$^Z$ have been defined above.

As used herein, a "guanidine" group refers to the structure —N═C(N(R$^X$R$^Y$))N(R$^X$R$^Y$) or —NR$^X$—C(═NR$^X$)NR$^X$R$^Y$ wherein R$^X$ and R$^Y$ have been defined above.

As used herein, the term "amidino" group refers to the structure —C═(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). In some examples, a straight aliphatic chain has the structure —[CH$_2$]$_v$—, where v is 1-12. In some examples, a branched aliphatic chain is a straight aliphatic chain that is substituted with one or more aliphatic groups. A branched aliphatic chain has the structure —[CQQ]$_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R$_1$, R$_2$, R$_3$, R$_4$, R$_5$, R$_6$, and X and other variables contained in formulae described herein encompass specific groups, such as alkyl and aryl. Unless otherwise noted, each of the specific groups for the variables can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl) carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom (s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as therapeutic agents.

II. Compounds

In one aspect, the invention provides a compound of Formula I:

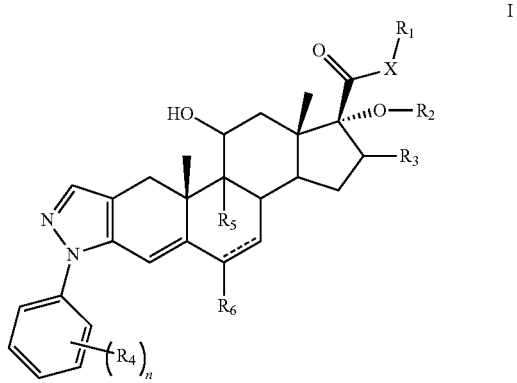

or a pharmaceutically acceptable salt thereof, wherein
X is —O— or —S—;
----- is a bond or is absent;
R$_1$ is selected from hydrogen, C$_{1-6}$ alkyl, cycloalkyl, aryl, heteroaryl, aralkyl, heteroaralkyl, or heterocycloalkyl, any of which is optionally substituted;
R$_2$ is -L-R'— wherein L is a bond or —C(O)— and R' is selected from hydrogen, C$_{1-6}$ alkyl, cycloalkyl, aryl, heteroaryl, aralkyl, heteroaralkyl, or heterocycloalkyl, wherein R' is optionally substituted;
R$_3$ is hydrogen or optionally substituted C$_{1-6}$ alkyl;
each R$_4$ is independently selected from hydrogen, C$_{1-6}$ alkyl, —OH, halo, haloalkyl, —CN, —NO$_2$, —C(O)(C$_{1-6}$ alkyl), —NHC(O)(C$_{1-6}$ alkyl), —OC(O)(C$_{1-6}$ alkyl), —C(O)NH(C$_{1-6}$ alkyl), —C(O)O(C$_{1-6}$ alkyl), —SO$_2$(C$_{1-6}$ alkyl), or —SO$_2$NH(C$_{1-6}$ alkyl), wherein R$_4$ is optionally substituted;

each of R$_5$ and R$_6$ is independently hydrogen, halo, or C$_{1-4}$ alkyl; and n is 0, 1, 2, 3, 4, or 5.

In some embodiments, R$_1$ is hydrogen, C$_{1-6}$ alkyl, cycloalkyl, or aryl, wherein the alkyl, cycloalkyl, or aryl is optionally substituted. For example, R$_1$ is alkyl, cycloalkyl, or aryl, any of which is optionally substituted with halo. In other examples, R$_1$ is hydrogen or C$_{1-6}$ alkyl, wherein the C$_{1-6}$ alkyl is optionally substituted with 1-3 halo. And, in some examples, R$_1$ is methyl, ethyl, propyl, isopropyl, butyl, isobutyl, or tert-butyl, any of which is optionally substituted with 1-3 halo. For instance, R$_1$ is fluoromethyl. In other examples, R$_1$ is unsubstituted C$_{1-6}$ alkyl. For instance, R$_1$ is methyl, ethyl, propyl, isopropyl, butyl, isobutyl, or tert-butyl. In some instances, R$_1$ is ethyl. In some instances, R$_1$ is isopropyl. In some instances, R$_1$ is tert-butyl. In some instances, R$_1$ is hydrogen. In some embodiments, R$_1$ is an optionally substituted 3-7 membered cycloalkyl, phenyl, or naphthyl, any of which is optionally substituted.

In some embodiments, L is —C(O)— and R' is hydrogen, C$_{1-6}$ alkyl, aralkyl, heteroaryl, or heteroaralkyl, wherein R$_2$ is optionally substituted with halo, CN, carboxyl, or oxo. For example, L is —C(O)— and R$_2$ is heteroaryl. In other examples, R$_2$ is

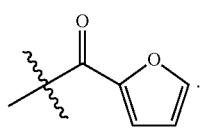 [SMILES: *C(=O)c1ccco1]

In some embodiments, R$_3$ is optionally substituted C$_{1-6}$ alkyl. For example, R$_3$ is methyl, ethyl, propyl, isopropyl, butyl, isobutyl, or tert-butyl, any of which optionally substituted. In other examples, R$_3$ is hydrogen.

In some embodiments, R$_4$ is independently selected from hydrogen, C$_{1-6}$ alkyl, —OH, halo, —CN, —NO$_2$, —C(O)(C$_{1-6}$ alkyl), —NHC(O)(C$_{1-6}$ alkyl), —OC(O)(C$_{1-6}$ alkyl), —C(O)NH(C$_{1-6}$ alkyl), or —C(O)O(C$_{1-6}$ alkyl), wherein the alkyl group of R$_4$ is optionally substituted with halo, —CN, carboxyl, or oxo. In some examples, each R$_4$ is independently selected from hydrogen, C$_{1-6}$ alkyl, halo, —CN, —NO$_2$, —C(O)(C$_{1-6}$ alkyl), —C(O)NH(C$_{1-6}$ alkyl), or —C(O)O(C$_{1-6}$ alkyl), wherein the alkyl group of R$_4$ is optionally substituted with halo, carboxyl, or oxo. And, in some examples, each R$_4$ is independently hydrogen, C$_{1-6}$ alkyl or halo. In other examples, each R$_4$ is hydrogen.

In some embodiments, R$_4$ is hydrogen and R$_1$ is hydrogen, C$_{1-6}$ alkyl, or haloalkyl.

In some embodiments, n is 0, 1, or 2. For example, n is 0.

In some embodiments, X is —O—.

In some embodiments, X is —S—.

In some embodiments, ----- is a bond.

In some embodiments, ----- is absent.

In some embodiments, R$_5$ and R$_6$ are each independently hydrogen or halo. For example, R$_5$ and R$_6$ are both —F.

In some embodiments, the compound of Formula I is selected from a compound in Table 1, below.

TABLE 1

Compounds of Formula I.

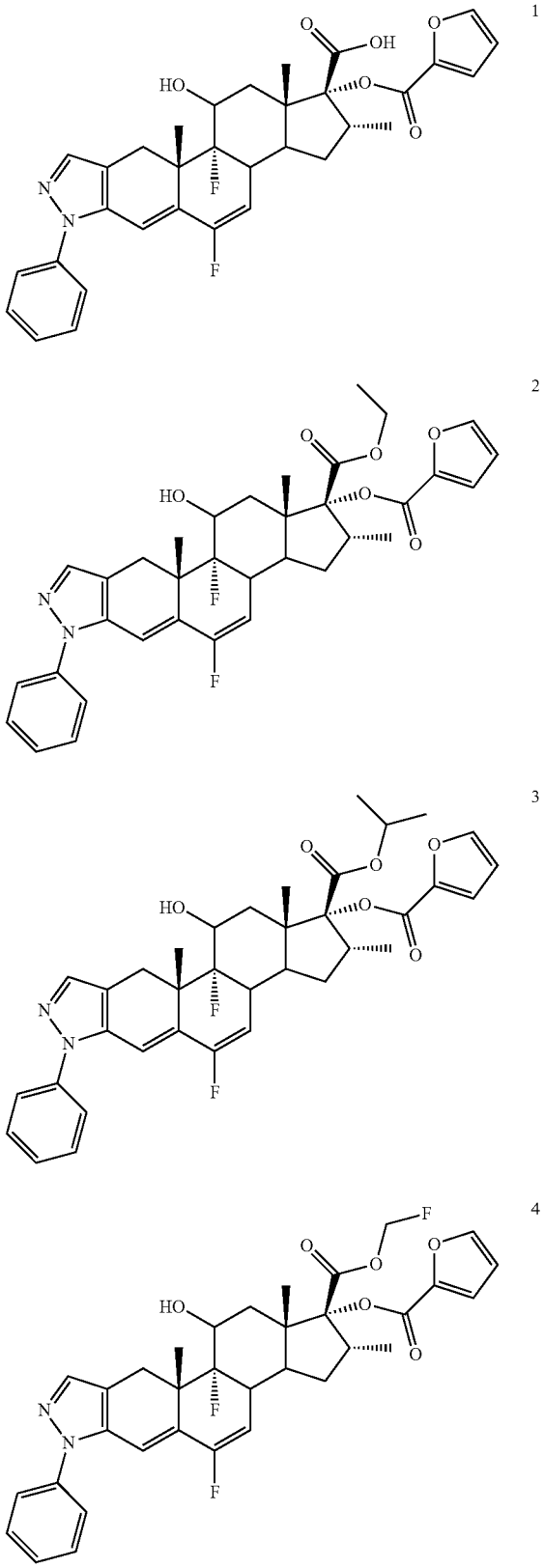

TABLE 1-continued

Compounds of Formula I.

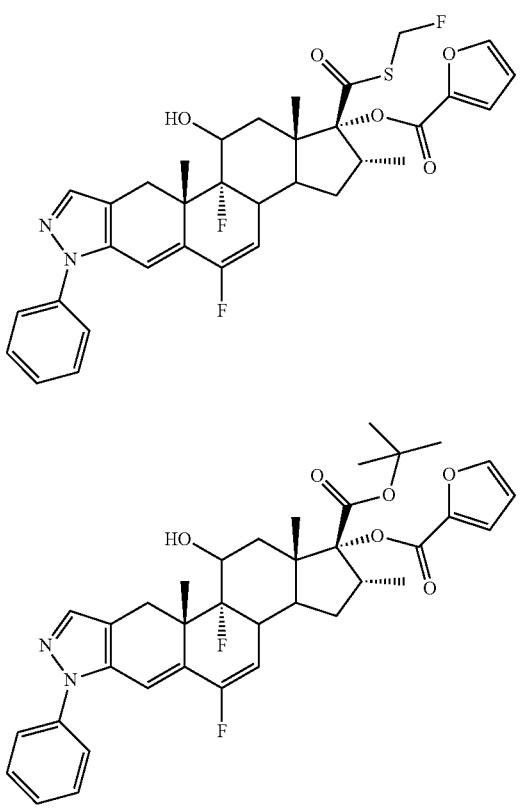

III. Pharmaceutically Acceptable Compositions

In one aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic cit using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, edisylate (ethanedisulfonate), ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

IV. Use and Administration of the Compounds

In another aspect, the present invention provides a method of treating or lessening the severity of inflammation in a subject, the method comprising administering an effective amount of a composition comprising a compound of Formula I to the subject, preferably a mammal, in need thereof. The present invention also provides a method of treating or lessening the severity of an inflammatory disease in a subject, the method comprising administering an effective amount of a composition comprising a compound of Formula I to the subject, preferably a mammal, in need thereof.

In yet another aspect, the present invention provides a method of treating or lessening the severity of a condition, disease, or disorder implicated by glucocorticoid receptor. In certain embodiments, the present invention provides a method of treating a condition, disease, or disorder implicated by a deficiency of glucocorticoid receptor activity, the method comprising administering an effective amount of a composition comprising a compound of Formula I to a subject, preferably a mammal, in need thereof. In certain embodiments, the present invention provides a method of treating an inflammatory condition, disease, or disorder in a subject, wherein the subject has normal glucocorticoid receptor activity, the method comprising administering an effective amount of a composition comprising a compound of Formula I to a subject, preferably a mammal, in need thereof.

In another aspect, the present invention provides a method of treating or lessening the severity of a condition, disease, or disorder implicated by glucocorticoid receptor, wherein the condition, disease, or disorder is selected from asthma, arthritis, lupus, Crohn's disease, Inflammatory bowel diseases, Coeliac disease, Glomerulonephritis, Acne vulgaris, leukemia, and pancreatic cancer.

According to the invention an "effective amount" of the compound or pharmaceutically acceptable composition is that amount effective for treating or lessening the severity of one or more of the diseases, disorders or conditions as recited above.

The compounds and compositions, according to the method of the present invention, may be administered using any amount and any route of administration effective for treating or lessening the severity of one or more of the diseases, disorders or conditions as recited above.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The activity of a compound utilized in this invention as a modulator of the glucocorticoid receptor may be assayed according to methods described generally in the art and in the Examples herein.

V. Examples

The examples provide herein are provided so that the invention may be more fully understood, and are not meant to be limiting in any way.

General Synthetic Schemes

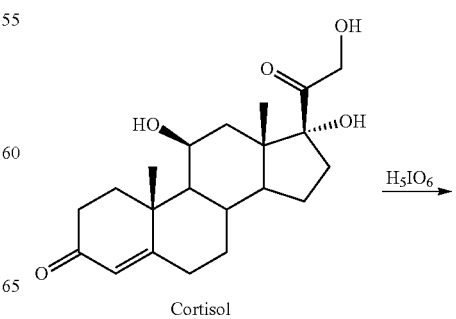

Scheme 1

Cortisol

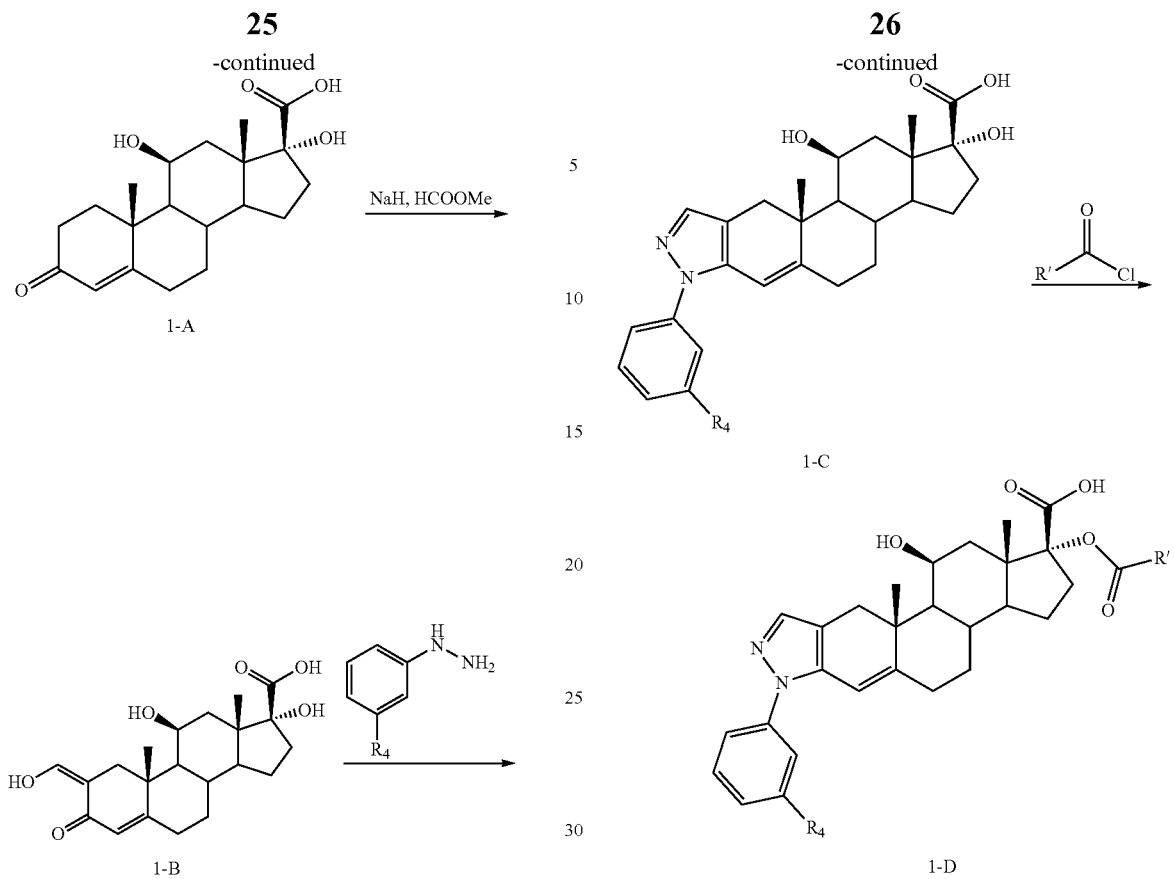
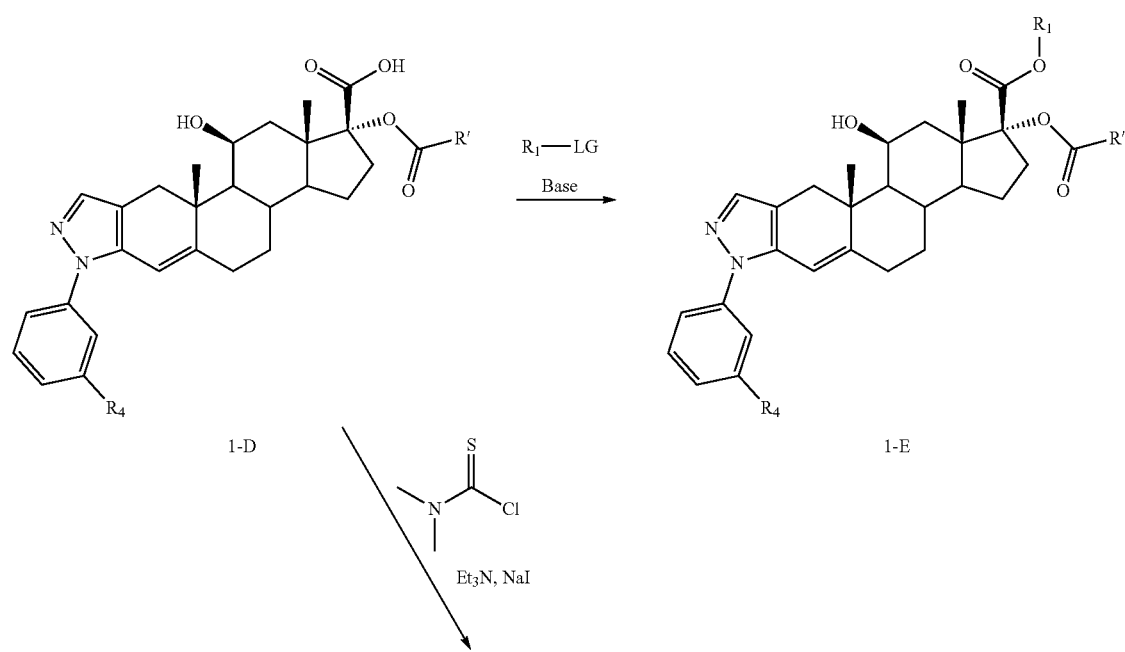
Scheme 2

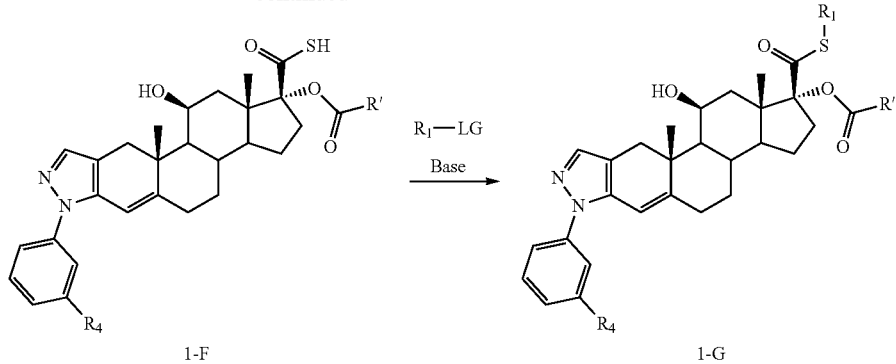

1-F → 1-G

Schemes 1 and 2 provide general synthetic syntheses of compounds of Formula 1-G from commercially available Cortisol, wherein $R_1$, $R_4$, and R' are defined above. From Scheme 1, oxidation of Cortisol with a reagent such as periodic acid provides a carboxylic acid of Formula 1-A, which can be further functionalized at a later stage in the synthesis. Treatment of 1-A with a base and aldehyde reagent, such as NaH/methyl formate conditions provides a compound of Formula 1-B. Treatment of 1-B with an optionally substituted phenyl hydrazine (Schemes 1 and 2 show a substituent in the meta position, for example) provides a compound of Formula 1-C. Functionalization of the 17α hydroxyl substituent with an acyl chloride of the structure

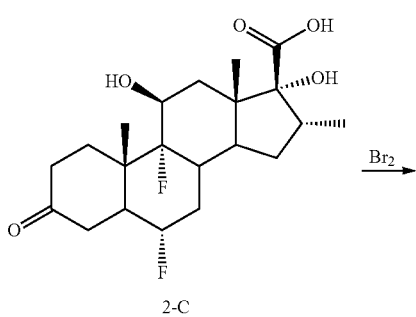

provides a compound of Formula 1-D.

Scheme 2 provides a general synthesis with respect to functionalization of the carboxylic acid moiety of a compound of Formula 1-D. To obtain an ester, a compound of Formula 1-D can be treated with a base and a compound of formula $R^1$-LG, wherein LG is a leaving group, to provide Formula 1-E. The thioester of 1-D can be obtained by first transformation of the carboxylic acid moiety with a suitable reagent, such as N, N-dimethylcarbamothioic chloride, to a thiocarboxylic acid of Formula 1-F, which can be further reacted with a compound of formula $R^1$-LG, wherein LG is a leaving group, to provide a compound of Formula 1-G.

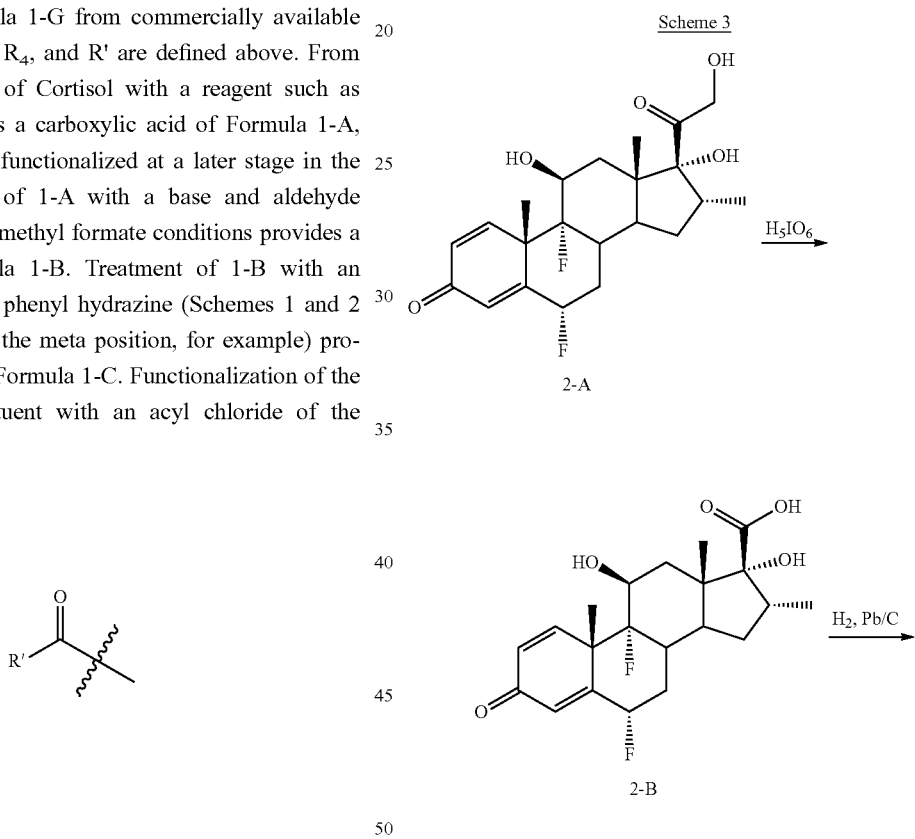

Scheme 3

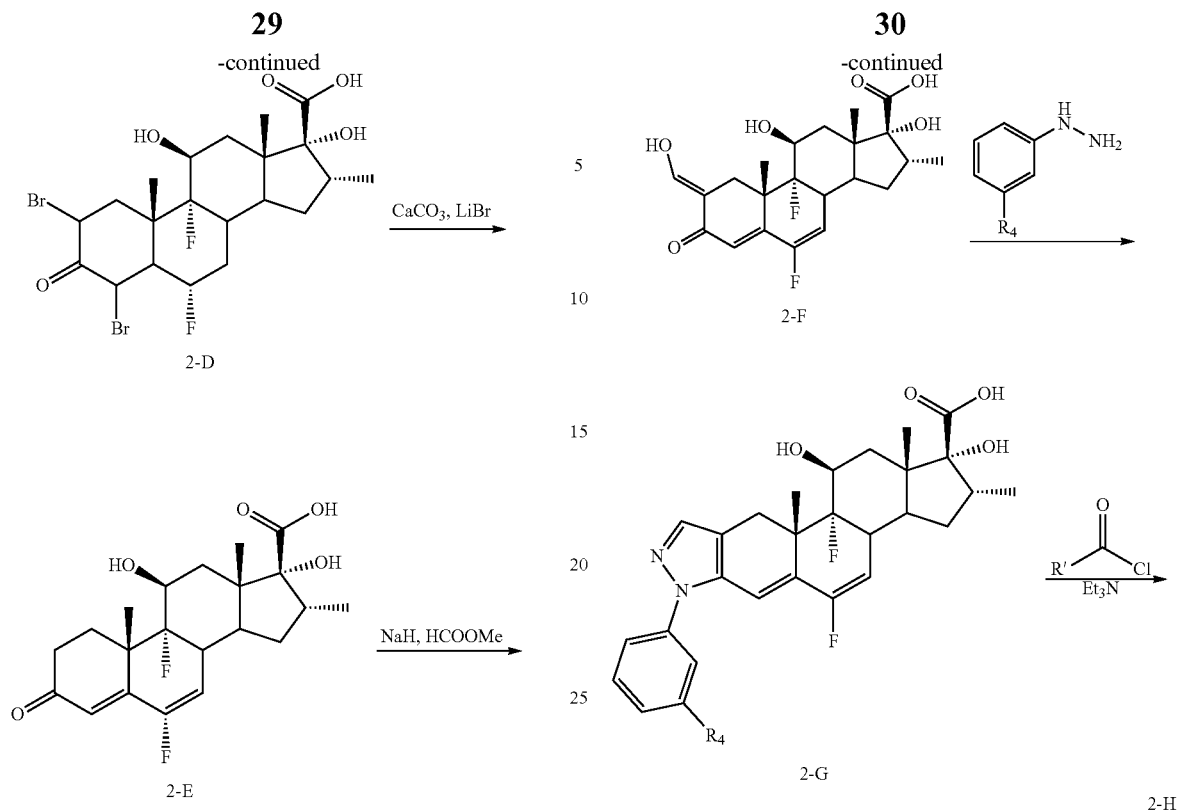
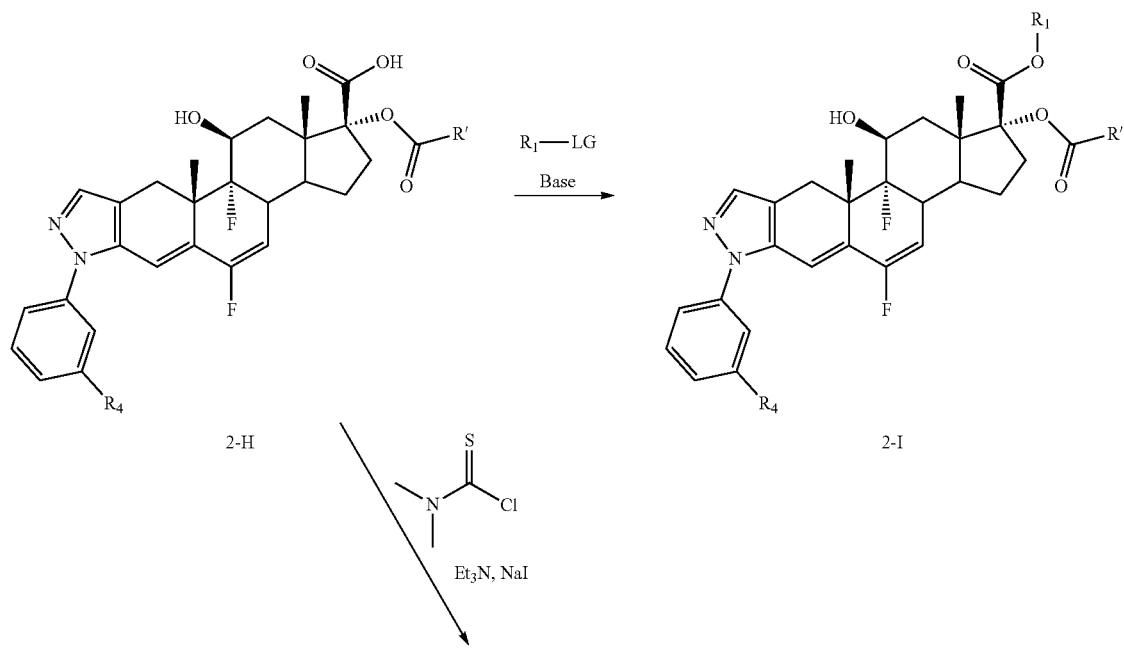
Scheme 4

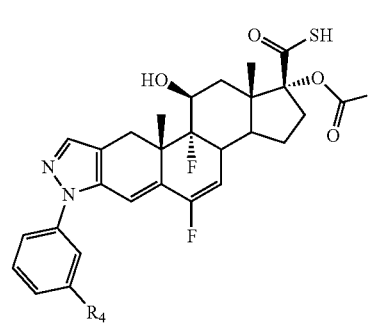

2-J

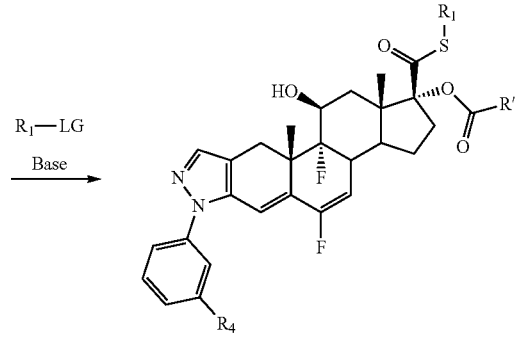

2-K

Compounds of Formula 2-I can be synthesized from starting compounds, such as 2-A, according to Schemes 3 and 4 above. The reaction steps, sequences of those steps, and reagents used are meant to be illustrative and are not meant to limit the invention in any way.

In accordance with Scheme 3, oxidative cleavage of the hydroxyl methyl group of the α-hydroxy acetyl group of 2-A to provide 2-B can be achieved using periodic acid. Reduction of the olefinic moieties of 2-B using, for example, hydrogen gas and a Pd/C catalyst provides the saturated product, 2-C. Subsequent bromination using, for example, molecular bromine provides the bis-α,α' bromide compound, 2-D. Double elimination of the bromide substituents using a base, such as calcium carbonate, and a catalyst, such as lithium bromide, provides 2-E. Generation of the enolate of 2-E can be accomplished with a base, such as sodium hydride, followed by nucleophilic addition of methyl formate can provide compound 2-F. The treatment of 2-F with an optionally substituted phenylhydrazine (Schemes 3 and 4 show a substituent in the meta position, for example) can provide the pyrazine compound 2-G. Subsequent esterification of the free hydroxyl group of 2-G using an activated carbonyl compound of the formula R'—C(O)—X, wherein X is a leaving group such as chloride, can provide a compound of Formula 2-H.

Scheme 4 provides a general synthesis with respect to functionalization of the carboxylic acid moiety of a compound of Formula 2-H. To obtain an ester, a compound of Formula 2-H can be treated with a base and a suitable electrophile, such as halo alkyl, to provide Formula 2-I. The thioester of 2-H can be obtained by first transformation of the carboxylic acid moiety with a suitable reagent, such as N,N-dimethylcarbamothioic chloride, to a thiocarboxylic acid of Formula 2-J, which can be further reacted with a compound of formula $R^1$-LG, wherein LG is a leaving group, to provide Formula 2-K.

Synthetic Examples

Synthesis of Compound 2-B:

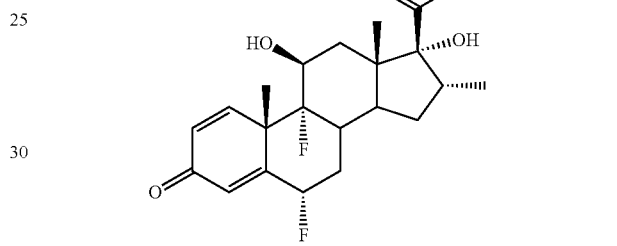

2-B

Commercially available Compound 2-A (4.1 g, 10 mmol) was dissolved in methanol (60 ml), and then periodic acid (4.5 g in 60 ml water, 20 mmol) was dropped at 0° C. The mixture was stirred at room temperature for 2 h. The methanol was concentrated and $H_2O$ (100 ml) was added. The precipitate was filtered, washed with water (15×3 ml), air dried to give compound 2-B (3.2 g) as a white solid. $^1$H NMR (400 MHz, DMSO) δ: 12.47 (s, 1H), 7.26 (dd, J=10.2, 1.2 Hz, 1H), 6.28 (dd, J=10.2, 1.9 Hz, 1H), 6.09 (s, 1H), 5.63 (ddd, J=48.5, 9.6, 6.7 Hz, 1H), 5.33 (dd, J=3.8, 1.7 Hz, 1H), 4.71 (s, 1H), 4.17-4.09 (m, 1H), 3.34 (s, 1H), 2.84 (ddd, J=11.1, 7.1, 4.1 Hz, 1H), 2.26-2.16 (m, 1H), 1.49 (s, 3H), 0.99 (s, 3H), 0.86 (d, J=7.1 Hz, 3H). LR-Mass (ESI) m/z: 397.1 $[M+H]^+$.

Synthesis of Compound 2-C:

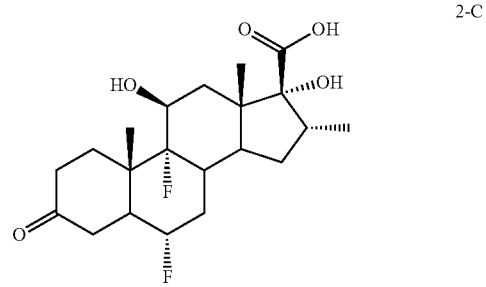

2-C

Compound 2-B (1.9 g, 5 mmol) was dissolved in methanol (200 ml) and Pb/C(200 mg) was added. After stirring at room temperature under $H_2$ for 1 d. The solution was filtered through a pad of Celite, and then concentrated under reduced pressure to give 2-C (1.8 g) for the further use without purification. $^1$H NMR (400 MHz, DMSO) δ: 5.20-4.99 (m, 1H), 4.93 (d, J=2.6 Hz, 1H), 4.21 (m, 1H), 2.89-2.77 (m, 1H), 2.56 (m, J=15.9 Hz, 1H), 1.24 (s, 3H), 0.93 (s, 3H), 0.86 (d, J=7.1 Hz, 3H). LR-Mass (ESI) m/z: 401.2 [M+H]$^+$.

Synthesis of Compound 2-D:

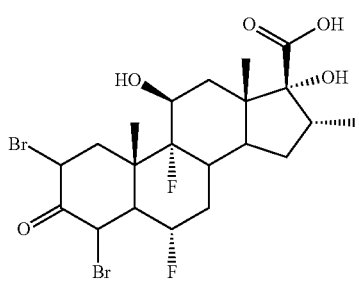

The Compound 2-C (1.6 g) in acetic acid (40 ml.) was treated successively with 6.6 M hydrogen bromide in acetic acid (1.6 ml) and a solution of bromine in acetic acid (4.5 ml.). After stirring at room temperature for 40 min. Dilution with water gave the crude 2-D (2.1 g). $^1$H NMR (300 MHz, DMSO) δ: 5.32-4.96 (m, 3H), 4.69 (m, 2H), 4.18 (m, 1H), 3.07 (m, 1H), 2.95 (m, 1H), 2.81 (s, 1H), 1.31 (s, 3H), 0.88 (s, 3H), 0.84 (d, J=7.1 Hz, 3H). LR-Mass (ESI) m/z: 559.1 [M+H]$^+$.

Synthesis of Compound 2-E:

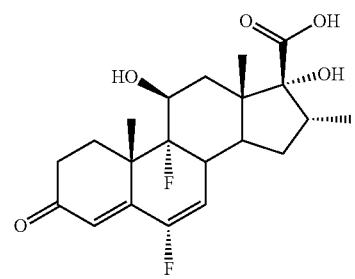

The Compound 2-D (2.0 g) was added to a vigorously stirred suspension of calcium carbonate (1.1 g) and anhydrous lithium bromide (0.8 g) in dimethylacetamide (17 ml) kept at 100° C. under nitrogen. After 3 hr, the cooled mixture was poured into an excess of dilute hydrochloric acid, the mixture was extracted with EtOAc, washed with brine, dried over Na$_2$SO$_4$. The crude product was purified by chromatography to give compound 2-E as a white solid to give a solid (0.6 g, 43%). $^1$H NMR (400 MHz, DMSO) δ: 5.85 (s, 1H), 5.62 (d, J=14.8 Hz, 1H), 5.27-5.19 (m, 1H), 4.74 (m, 1H), 4.11 (m, 1H), 3.07-2.78 (m, 3H), 2.70-2.58 (m, 1H), 2.42-2.03 (m, 6H), 1.45 (s, 3H), 1.03 (s, 3H), 0.89 (d, J=7.1 Hz, 3H). LR-Mass (ESI) m/z: 397.1 [M+H]$^+$.

Synthesis of Compound 2-F:

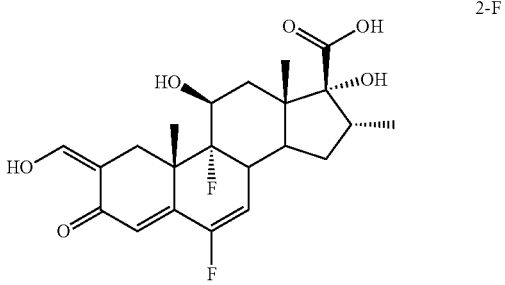

Compound 2-E (0.5 g) was dissolved in dry toluene (15 ml) and methyl formate (2 ml). Then, NaH (900 mg, 20 mmol, 60% dispersion in mineral oil) was added. After stirring at room temperature for 4 h, 1N HCl (120 ml) was added and the mixture was extracted several times with EtOAc. The solvent was dried and removed to give 0.6 g of 2-F as yellow foam for the further use without purification. LR-Mass (ESI) m/z: 425.3 [M+H]$^+$.

Synthesis of Compound 2-G-1:

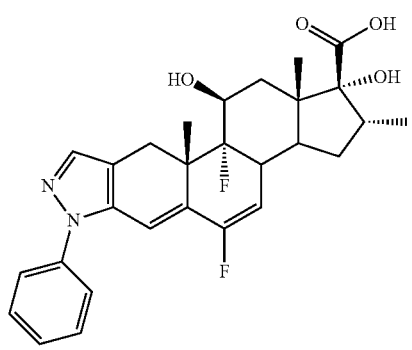

Compound 2-F (0.50 g) was dissolved in AcOH (15 ml) and H$_2$O (3 ml), phenylhydrazine (0.14 g) was added. The mixture was stirred at room temperature for 4 h. Cold water (100 ml) was added, The precipitate was filtered, washed with H$_2$O (10×3 ml), air dried to give compound 2-G-1 (0.44 g) as a yellow solid. $^1$H NMR (400 MHz, DMSO) δ: 7.61 (s, 1H), 7.58-7.49 (m, 4H), 7.42 (m, 1H), 6.54 (s, 1H), 5.33-5.20 (m, 2H), 4.16 (s, 1H), 2.38-2.29 (m, 1H), 2.10 (d, J=14.1 Hz, 1H), 1.71 (q, J=11.5 Hz, 1H), 1.53 (d, J=13.7 Hz, 1H), 1.26 (s, 3H), 1.05 (s, 3H), 0.87 (d, J=7.1 Hz, 3H). LR-Mass (ESI) m/z: 497.3 [M+H]$^+$.

Example 1: Synthesis of Compound 1

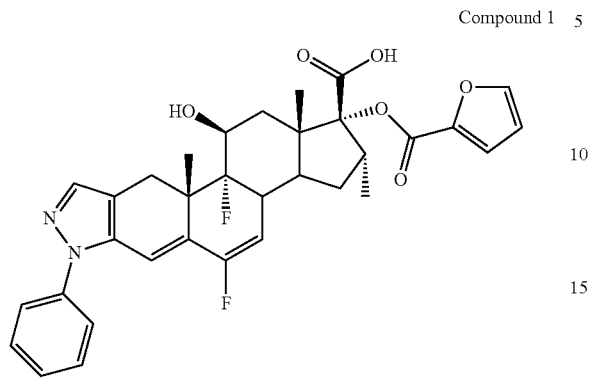

Compound 1

To a solution of compound 2-G-1 (400 mg, TEA (300 mL) in dry DCM (10 mL) was added α-Furoyl chloride (200 mg) at 0° C. under $N_2$. The mixture was stirred at room temperature for 30 min. The solvent was evaporated under reduced pressure to give the crude product which was purified by chromatography with DCM:MeOH (50:1) to give compound 1 as a white solid (82%). $^1$H NMR (400 MHz, DMSO) δ: 8.01-7.98 (m, 1H), 7.64 (s, 1H), 7.60-7.51 (m, 5H), 7.45 (m, 1H), 7.16 (dd, J=3.5, 0.6 Hz, 1H), 6.70 (dd, J=3.5, 1.7 Hz, 1H), 6.59 (s, 1H), 5.38 (dd, J=21.7, 8.8 Hz, 2H), 4.26 (s, 1H), 1.29 (s, 3H), 1.23 (s, 2H), 1.11 (s, 3H), 0.92 (d, J=7.1 Hz, 3H). LR-Mass (ESI) m/z: 591.2 [M+H]$^+$.

Example 2: Synthesis of Compound 2

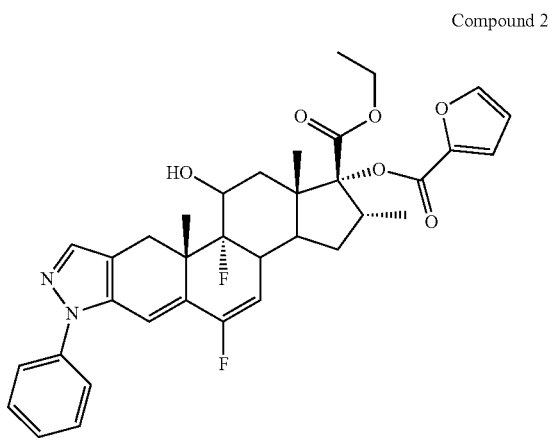

Compound 2

Compound 1 (50 mg) was added to a vigorously stirred suspension of potassium carbonate (30 mg) and iodoethane (20 mg) in DMF (2 mL), and the resulting mixture was stirred at 50° C. for 3 hr. The reaction solution was poured into water (30 mL) and extracted with EtOAc (20 mL×3), the combined organic layer washed with brine, dried over $Na_2SO_4$. The crude product was purified by Prep-TLC to give compound 2 as a white solid (41 mg, 79%). $^1$H NMR (400 MHz, DMSO) δ: 8.00 (s, 1H), 7.65 (s, 1H), 7.61-7.51 (m, 4H), 7.45 (m, 1H), 7.19 (d, J=3.6 Hz, 1H), 6.71 (dd, J=3.2, 1.6 Hz, 1H), 6.58 (s, 1H), 5.47-5.28 (m, 2H), 4.27 (s, 1H), 4.23-4.06 (m, 2H), 1.20 (t, 3H). LC-MS (ESI) m/z: 619.3 [M+H]$^+$.

Example 3: Synthesis of Compound 3

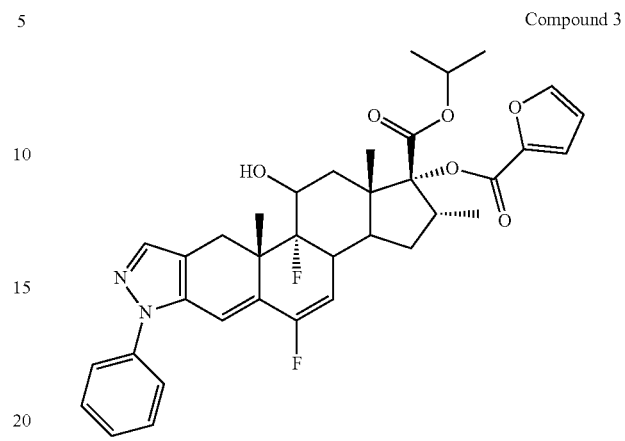

Compound 3

Compound 1 (50 mg) was added to a vigorously stirred suspension of potassium carbonate (30 mg) and 2-bromopropane (15 mg) in DMF (2 mL) and the resulted mixture was stirred at 50° C. for 3 hr. The reaction solution was poured into water (30 mL) and extracted with EtOAc (20 mL×3), the combined organic layer washed with brine, dried over $Na_2SO_4$. The crude product was purified by Prep-TLC to give compound 3 as a white solid (39 mg, 73%). $^1$H NMR (400 MHz, CDCl3) δ: 7.58 (s, 1H), 7.54-7.47 (m, 6H), 7.38 (m, 1H), 7.15 (d, J=3.6 Hz, 1H), 6.75 (s, 1H), 6.48 (dd, J=3.2, 1.6 Hz, 1H), 5.25-5.08 (m, 2H), 4.45 (s, 1H), 1.31 (d, 3H), 1.23 (d, 3H). LC-MS (ESI) m/z: 633.3 [M+H]$^+$.

Example 4: Synthesis of Compound 4

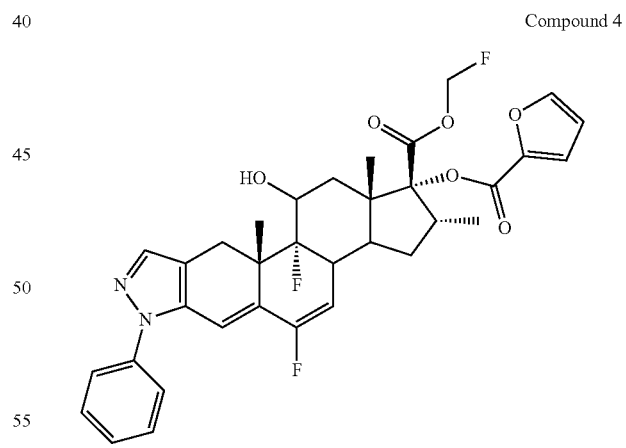

Compound 4

Compound 1 (50 mg) was added to a vigorously stirred suspension of potassium carbonate (30 mg) and fluoro-iodo-methane (15 mg) in DMF (2 mL), and the resulting mixture was stirred at 50° C. for 3 hr. The reaction solution was poured into water (30 mL) and extracted with EtOAc (20 mL×3), the combined organic layer washed with brine, dried over $Na_2SO_4$. The crude product was purified by Prep-TLC to give compound 4 as a white solid (38 mg, 72%). $^1$H NMR (400 MHz, DMSO) δ: 8.02 (s, 1H), 7.65 (s, 1H), 7.63-7.50 (m, 4H), 7.45 (m, 1H), 7.25 (d, J=3.6 Hz, 1H), 6.73 (dd, J=3.2, 1.6 Hz, 1H), 6.60 (s, 1H), 5.84 (d, J=112.4 Hz, 1H), 5.83 (d, 1H), 5.54 (d, 1H), 5.37 (d, 1H), 4.28 (s, 1H). LC-MS (ESI) m/z: 623.2 [M+H]$^+$.

Example 5: Synthesis of Compound 5

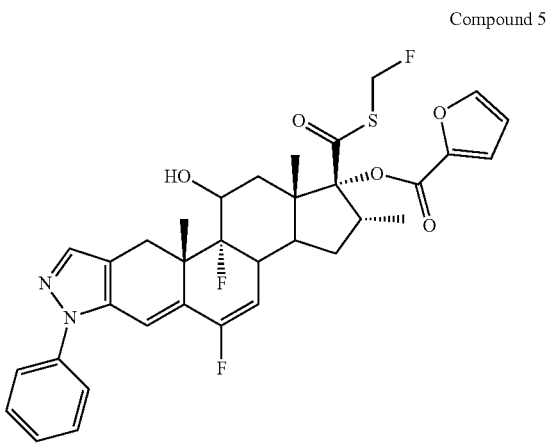

Compound 5

Part I: To a stirred solution of compound 1 (200 mg) in 2-butanone (5 mL) were added N, N-dimethylcarbamothioic chloride (83 mg), triethylamine (100 mg), and sodium iodide (5 mg). The mixture was stirred at 75° C. for 2 hr and was then concentrated in vacuo. The obtained residue was washed with water and dried to yield 0.2 g of the product. The obtained compound was added to morpholine (3 mL) and the obtained mixture was stirred at room temperature overnight. Then, a mixture of water and ethyl acetate at 10-15° C. was added into the above reaction solution. Finally, glacial acetic acid (0.5 mL) was added drop wise to adjust the pH to a pH 5-7. The precipitated solid was filtered, washed with water, and dried to give 170 mg of (1R,2R,10aS,10bR,11S,12aS)-5,10b-difluoro-1-((furan-2-carbonyl)oxy)-11-hydroxy-2,10a,12a-trimethyl-7-phenyl-1,2,3,3a,3b,7,10,10a,10b,11,12,12a-dodecahydrocyclopenta[5,6]naphtho[1,2-f]indazole-1-carbothioic S-acid (Compound 2-J-1), which was used in next step directly.

Part II: Compound 2-J-1 (50 mg) was added to a vigorously stirred suspension of potassium carbonate (30 mg) and fluoro-iodo-methane (15 mg) in DMF (2 mL), and the resulted mixture was stirred at 50° C. for 3 hr. Then the obtained solution was poured into water (30 mL) and extracted with EtOAc (20 mL×3), the combined organic layer washed with brine, dried over Na$_2$SO$_4$, then concentrated and purified by Prep-TLC to give compound 5 as a white solid (35 mg, 66%). $^1$H NMR (400 MHz, DMSO) δ: 8.05 (s, 1H), 7.65 (s, 1H), 7.61-7.51 (m, 4H), 7.45 (m, 1H), 7.25 (d, J=3.6 Hz, 1H), 6.74 (dd, J=3.2, 1.6 Hz, 1H), 6.60 (s, 1H), 6.04 (s, 1H), 5.92 (s, 1H), 5.54 (s, 1H), 5.39-5.31 (m, 1H), 4.28 (s, 1H). LR-Mass (ESI) m/z: 639.2 [M+H]$^+$.

Example 6: Synthesis of Compound 6

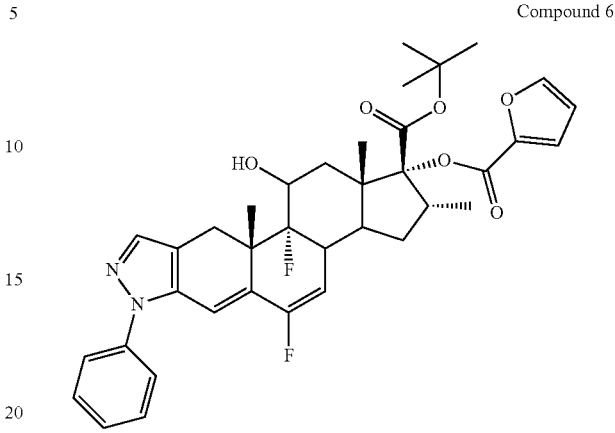

Compound 6

Compound 1 (180 mg) was added to a vigorously stirred suspension of potassium carbonate (200 mg) and 2-bromo-2-methylpropane (10 mL) in DMF (5 mL), and the resulting mixture was stirred at room temperature for 8 days. The reaction solution was poured into water (30 mL) and extracted with EtOAc (20 mL×3), the combined organic layer washed with brine, dried over Na$_2$SO$_4$. The crude product was purified by Prep-TLC to give compound 6 as a white solid (11 mg, 5.6%). $^1$H NMR (400 MHz, CDCl3) δ: 7.58 (s, 1H), 7.54-7.46 (m, 6H), 7.38 (m, 1H), 7.13 (d, J=3.2 Hz, 1H), 6.75 (s, 1H), 6.48 (dd, J=3.2, 1.6 Hz, 1H), 5.22 (d, H), 4.45 (s, 1H), 1.50 (s, 9H). LC-MS (ESI) m/z: 647.3 [M+H]$^+$.

Methods and Materials

Example 7A: Protein Expression and Purification

The GR LBD (residues 525-777) containing mutations F602A, C622Y, T668V, S674T, V675I, K699A, and K703A for Mometasone Furoate and mutations F602A, C622Y, T668V, S674T, V675I, E684A, and E688A for Cortisol were expressed as a 6×His-GST fusion protein from the expression vector pET24a (Novagen). The modified fusion proteins contain a His6-tag (MKKGHHHHHHG) at the N terminus and a thrombin protease site between GST and the GR LBD. BL21DE3 cells transformed with the expression plasmids were grown in LB broth at 16° C. to an OD600 of ~1 and induced with 0.1 mM IPTG and 50 μM Mometasone Furoate or Cortisol. Cells were harvested, resuspended in 200 ml extract buffer (50 mM Tris[pH8], 150 mM NaCl, 2 M urea, 10% glycerol+1 μM ligand) per 12 liters of cells, and passed three times through a French Press with pressure set at 1000 Pa. The lysate was centrifuged at 20,000 rpm for 30 min, and the supernatant was loaded on a 25 ml nickel column. The column was washed with 700 ml extract buffer and eluted with 300 ml of 50% Buffer B (25 mM Tris [pH8], 500 mM Imizadole, 10% glycerol, 1 μM ligand). The GR LBD was cleaved overnight with thrombin at a protease/protein ratio of 1:1000 in the cold room while being dialyzed against 20 mM Tris [pH8], 500 mM NaCl, 10% glycerol, 1 μM ligand. The H6GST tag was removed by binding to a Ni-NTA nickel column. The flow through was further purified by gel filtration (20 mM Tris [pH8], 500 mM NaCl.1 mM DTT, 1 mM EDTA, 10% glycerol, 1 μM ligand). The Mometasone Furoate bound protein was complexed with the longer version SRC2-3 peptide: SPKKKENALLRYLL-DKDDTKD and filter concentrated to 6 mg/ml. The Cortisol GR LBD was complexed with the shorter version SRC2-3: KENALLRYLLDKDD and 0.2% B-octyl glucoside and filter concentrated to 7 mg/ml.

Example 7B: Crystallization

The Mometasone Furoate GR crystals were grown at room temperature in hanging drops containing 1 μl of the protein complexed with GP2 peptide and 2 μl of the well solution containing 0.1 M sodium citrate [pH6] and 2.2 M sodium chloride. The cortisol GR crystals were grown at room temperature in hanging drops containing 1 μl of the protein complex and 1 μl of the well solution containing 0.1M imidazole pH6.5, 1M sodium acetate trihydrate. 30% sucrose in the well buffer was used as a cryoprotectant for both.

Example 7C: Structure Determination

The CCP4 program PHASER was used for molecular replacement (36), with the GR LBD/dexamethasone structure (PDB code: 1M2Z) (27) as the search model. The initial model was manually rebuilt and refined using CNS (37) and the CCP4 program REFMAC5 (38). All structure figures were prepared using PyMOL (The PyMOL Molecular Graphics System, Version 1.3, Schrödinger LLC).

Example 7D: Cell Transfection and Reporter Assays

AD293 cells were split at 20,000/well in 24 well plate one day before transfection. For transactivation, 100 ng pHHLuc (MMTV-Luc) plasmid, 0.1 ng pRShGR together with 5 ng phRGtkRenilla were transfected by X-tremeGENE 9 (Roche) into AD293 cells per well. For transreperssion, 10 ng AP1-Luc, 100 ng pRShGR and 5 ng phRGtkRenilla were transfected into AD293 cells per well. One day after transfection, cells were induced by different treatment (steroids or vehicle) 16 hrs overnight. Cells were harvest by 1× passive lysis buffer (Promega), luciferase activity was assayed by the Dual-Glo Luciferase system (Promega). Data were plotted by Luciferase Value/Renilla Value, as Relative Luciferase Unit (RLU).

Example 7E: In Vitro GR Ligand Binding Assay

In vitro GR binding assay is similar as described before (39). Radiolabeled ligand [$^3$H]Dex was fixed at 25 nM, and incubated with 5% GR cytosol plus 20 mM sodium molybdate in TAPS buffer (ph8.8), cold ligand (varying from 0.1 nM to 10 μM) were added to compete hot-ligand binding. Data were plotted as a standard competition curve by GraphPad Prism 5.

Biological Examples

Example 8: Overall Structure of the Cortisol- and MF-Bound GR LBDs

Crystallization of the GR LBD has always been a challenge due to its solubility problem. The original GR LBD structure was determined with a high affinity ligand DEX (27), bound to the GR LBD with F602S mutation, which improve protein solubility. However, cortisol is a much weaker ligand than DEX and the F602S mutation is not sufficient for stabilizing the GR LBD bound to cortisol, an endogenous hormone (FIG. 8, lane 1). To identify amino acids that might increase GR LBD solubility without affecting overall structure, we aligned GR with the closest members of steroid hormone family, MR, androgen receptor (AR) and progesterone receptor (PR), which are much more soluble than GR. Besides F602, residue C622, T668, S674 and V675 distinguish from the conserved sequences of the family, so the inventors mutated those amino acids back to the conserved residues (F602A, C622Y, 1668V, S674T and V675I, termed AYVTI). Most of these residues are found inside of proteins with the PR residues having better packing in the PR LBD structure (28). Indeed, the AVYTI GR LBD has much better solubility than the F602S LBD when bound to cortisol (FIG. 8, lane 2). The mutated GR LBD can be expressed and purified with a yield greater than 5 mg per liter. However, the inventors were not able to obtain crystals of this mutated GR LBD bound to cortisol or MF. The GR LBD has several lysine and glutamic acid residues in its helix H9, whose long side chains may affect crystallization. The GR LBD with alanine mutations of these residues (K669A/K703A for MF and E684A/E688A for cortisol) as surface entropy reduction mutations remained soluble (FIG. 8, lanes 3 and 4) and allowed us to obtained crystals of the GR LBD bound to MF and cortisol (FIGS. 9A-B). All these mutations are far away from the ligand binding pocket and do not alter ligand-mediated GR transactivation or transrepression functions (FIGS. 10A-B).

The overall structures of the MF-bound and cortisol-bound GR LBDs (FIG. 1A) are similar to the DEX-bound GR LBD, with 11 helices packing into three layers of a helical sandwich bundle, with the ligand-binding cavity buried in the lower part of the bundle. The statistics of data collection and refinement are summarized in Table S1. The overall architecture of cortisol-bound GR LBD is almost identical as DEX-bound GR LBD, whereas there are some notable differences between MF-bound GR LBD and DEX-bound GR LBD, including the orientation of the loop before helix 1 (labeled "1" in FIG. 1B); an expansion of the loop region between helices 5 and 6 (labeled "2" in FIG. 1B); and a change in the C-terminal orientation of the AF-2 helix (labeled "3" in FIG. 1B). The ligand binding mode of cortisol and MF are well defined by clear electron density map of the bound ligands and the surrounding pocket residues (FIG. 1C).

TABLE 2

Statistics of data sets and structure refinement.

| | GR/Cortisol | GR/Mometasone |
|---|---|---|
| PDB code | 4P6X | 4P6W |
| Data collection | | |
| APS beam line | APS-21ID | APS-21ID |
| Space group | P61 | P23 |
| Resolution, Å | 30-2.5 | 30-1.95 |
| Cell parameters, Å, ° | a = b = 220.8, c = 74.2; α = β = 90, γ = 120 | a = b = c = 130.2; α = β = γ = 90 |
| Total/Unique reflections | 650426/71878 | 545016/53521 |
| Completeness, % | 100 (100) | 99.4 (98.0) |
| I/σ | 19.9 (5.2) | 23.5 (2.0) |
| Redundancy | 9.0 (7.6) | 10.2 (3.7) |
| Rsym | 0.10 (0.32) | 0.128 (0.51) |
| Structure determination | | |
| Resolution, Å | 40-2.5 | 30-195 |
| No. reflections | 71517 | 53320 |
| NCS molecules | 6 | 1 |

TABLE 2-continued

Statistics of data sets and structure refinement.

|  | GR/Cortisol | GR/Mometasone |
|---|---|---|
| No. residues | 1362 | 264 |
| No. solvent molecules | 487 | 130 |
| No. of non-H atoms | 13695 | 2315 |
| $R_{cryst}$ | 24.9% | 20.8% |
| $R_{free}$ | 29.2% | 22.7% |
| rmsd bonds, Å | 0.004 | 0.008 |
| rmsd angles, ° | 0.886 | 1.671 |
| Average B factor, Å$^2$ | 53.0 | 33.5 |
| Ramachandran statistics | Favored 94.6%, Allowed 4.5%, | Favored 97.7%, Allowed 2.3%, |

Rmsd is root-mean-square deviation from ideal geometry of protein.

Example 9: Potency, Affinity of Cortisol, DEX and MF

Figure 2A:
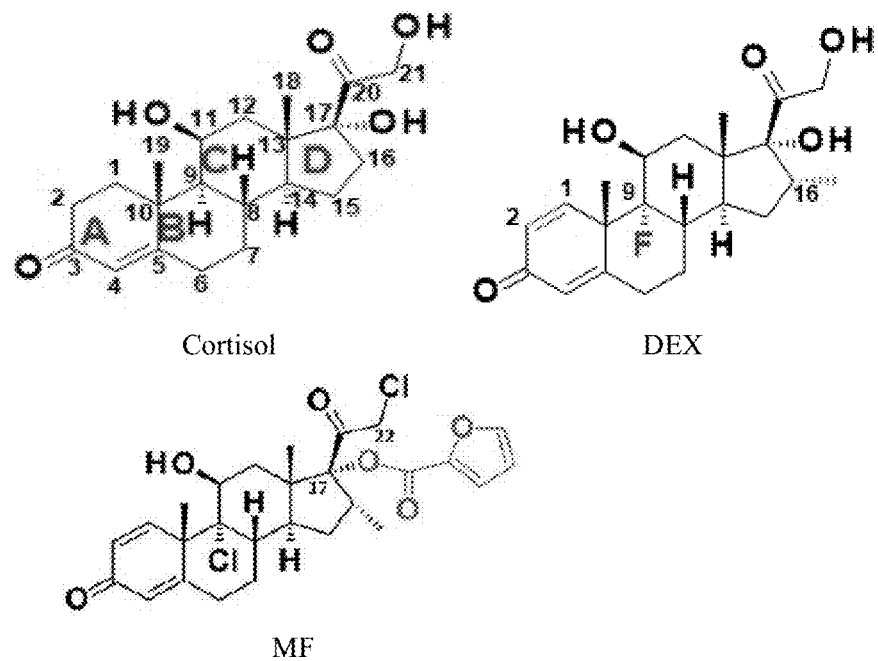
Figure 2B:
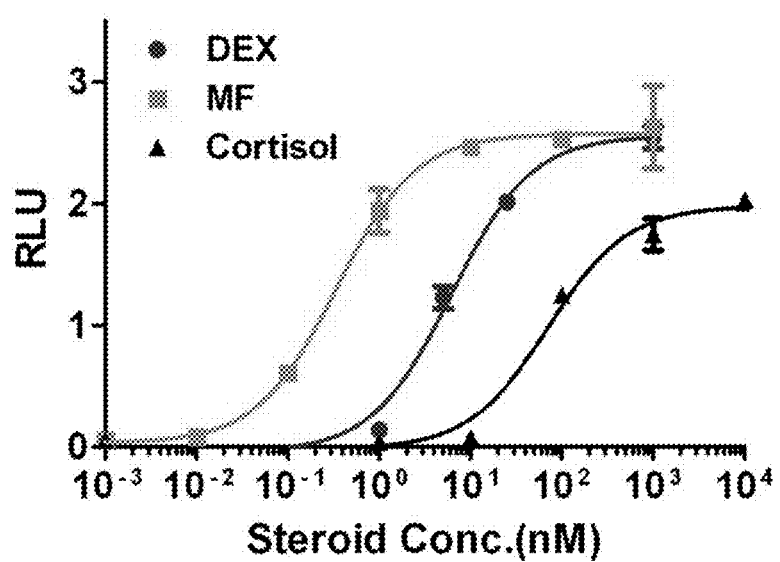

The change of chemical structures (FIG. 2A) of cortisol, DEX and MF silhouettes the evolution of glucocorticoid: from simple to complex and from one level to multiple levels. The cortisol structure provides a basic 4 ring steroid backbone; then DEX adds 1,2 double bone, 16 methylation and 9α halogenation (FIG. 2A); and MF further chloridizes at 22, and more importantly, adds a lipophilic furoate ester group at 17α (FIG. 2A), replacing the hydroxyl group of DEX and cortisol. To test the effects of those chemical changes on GR potency, the inventors side by side compared MF, DEX, and cortisol activities on both GR transactivation and transrepression in the format of full dose-response curve. For transactivation, the inventors used an MMTV-driven luciferase reporter system (FIG. 2B). MF and DEX showed almost the same efficacy (maximal activity) at the saturation concentration (1 μM), whereas cortisol at its saturation concentration (10 μM) had only 80% of the efficacy of DEX. Relative to DEX, there was a large leftward shift of the MF dose-response curve, indicating that MF is 20-fold more potent than DEX. On the other hand, the cortisol curve had a large rightward shift, showing it to be 10-fold less potent than DEX. The EC50 values for MF, DEX, and cortisol in transactivation were 0.33 nM, 6.7 nM, and 70 nM, respectively.

Figure 2C:
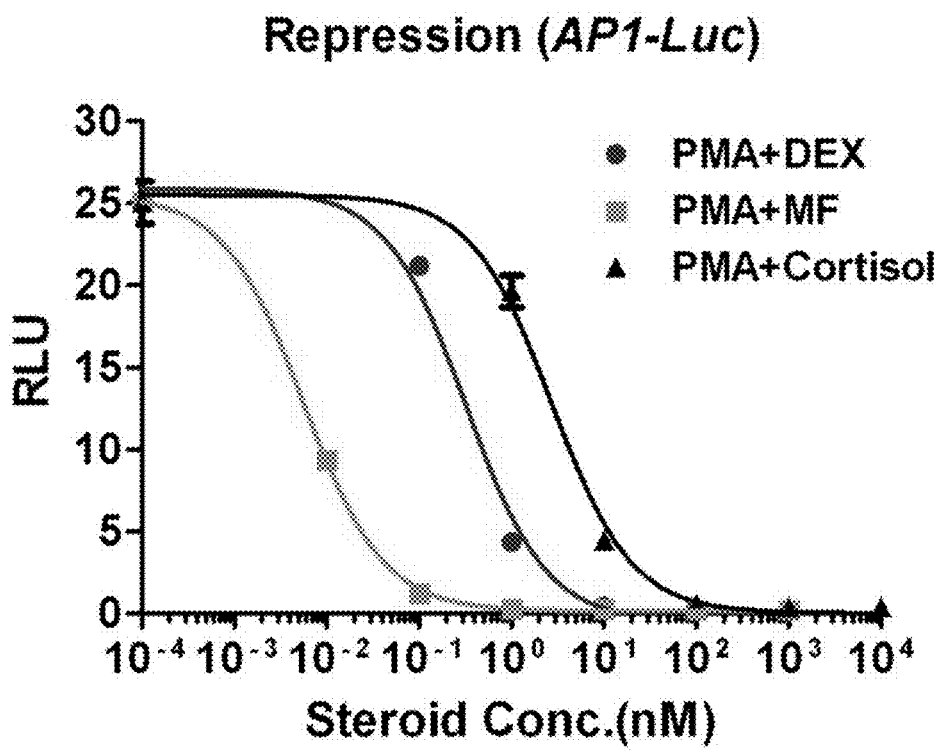
Figure 2D:
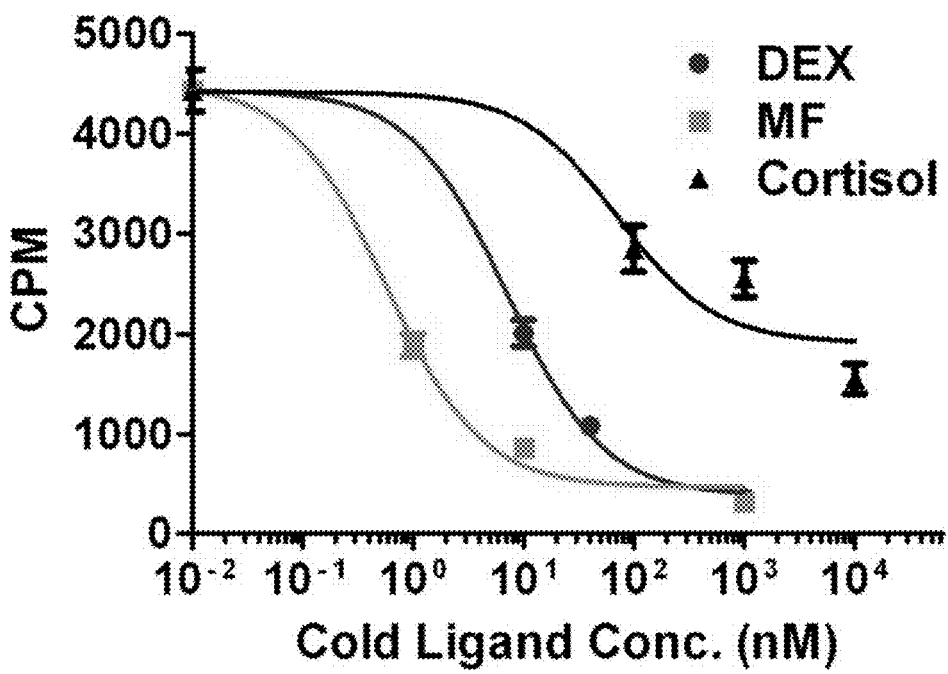

For transrepression, an AP1-driven luciferase reporter was used (FIG. 2C). MF, DEX, and cortisol showed similar efficacies at their saturation concentration. Again, MF showed much higher (60-fold) potency than DEX, and cortisol was much weaker than DEX; the $EC_{50}$ values for MF, DEX, and cortisol in transrepression were 0.005 nM, 0.32 nM, and 2.7 nM, respectively. Consistent with the frequent observation that induction requires a higher steroid concentration, the induction potency was at least 10-fold lower than the repression potency for each compound. This difference provides an opportunity to dissociate transactivation from transrepression via the use of very low doses of glucocorticoid. For example, at 0.1 nM, MF reaches 95% of transrepression efficacy but only 25% of transactivation efficacy (FIGS. 2B and 2C).

Generally, high potency is determined by a high affinity for the receptor, but cellular cofactors also play important roles. To test the affinity of MF for GR, the inventors performed in vitro GR ligand binding competition assays for MF, DEX, and cortisol (FIG. 2D), which showed that the order of GR binding affinity was MF>DEX>cortisol. The Ki values for MF, DEX, and cortisol were 0.7 nM, 8 nM, and 91 nM, respectively. This result was consistent with the inventor's result for potency. However, the difference in in vitro binding IC50 between MF and DEX was only about 10-fold, while the difference in potency was much more: 20-fold for induction and 60-fold for repression (FIGS. 2B and 2C). The other component of the difference in potency must be contributed by interactions with cellular factors that recognize the surface conformational changes caused by the binding of different ligands.

Example 10: The Flexibility of 1,2 Single Bond Attributed to the Low Affinity of Cortisol to GR To understand the underlying mechanism of the low affinity of cortisol, the inventors did a structural comparison of cortisol-bound GR LED and DEX-bound GR LED. The overall structure of cortisol-bound GR LED is almost exactly same as DEX-bound GR LED, there is no notable conformation change. Then the inventors looked into the detail of ligand binding. As mentioned above, DEX differentiate from cortisol only via: 1,2 double bond, 9α halogenation and 16 methylation (FIG. 2A), The C1-C2 double bond of DEX causes the steroid A ring and the C3-ketone group to become planar, thus allowing the C3-ketone to readily interact with R611 and Q570 (FIG. 3A). In contrast, because of the flexibility of the cortisol C1-C2 single bond, the steroid A ring needs to bend to form a hydrogen bond with R611 and Q570. Also, since the C1-C2 single bond of unbound cortisol oscillates between two conformations (above and below the A-ring plane), a water molecule is required to form a hydrogen bond network to hold the ligand in position. These observations explained the relatively low affinity of cortisol to GR. To confirm the importance of the C1-C2 double bond, we measured the potency of prednisolone, which differs from cortisol only by addition of the C1-C2 double bond (FIG. 3B, brown color), in a transactivation assay. Indeed, the C1-C2 double bond of prednisolone caused an about 5-fold leftward shift of the cortisol dose-response curve (FIG. 3B) and may therefore account for more than half of the total leftward shift caused by DEX. The remaining increase of potency is likely due to the C-9α halogenation and the C-16 methylation, both of which increase the interaction surface within the receptor pocket (FIGS. 11A-B).

Example 11: The 17α Furoate Determined the High Affinity of MF

Figure 4A:
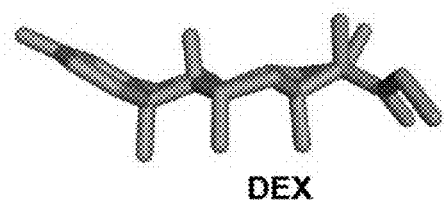
Figure 4B:
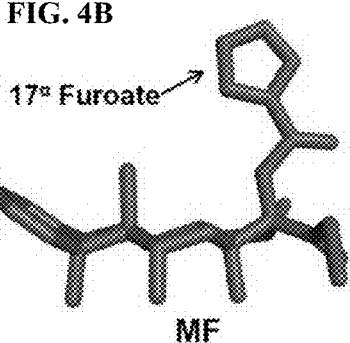
Figure 4C:
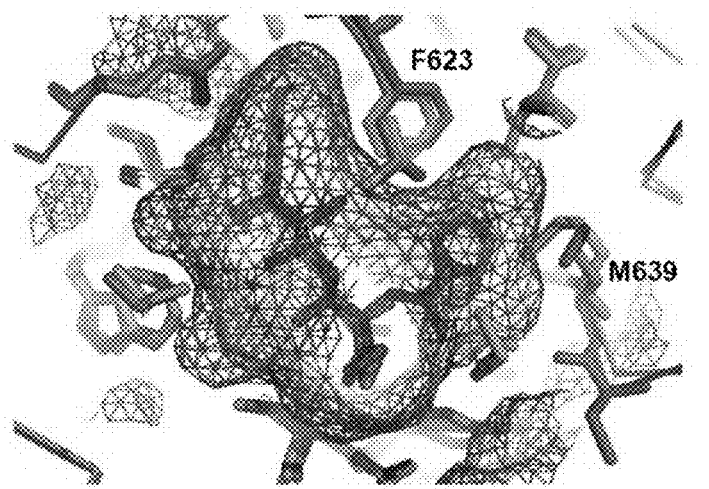
Figure 4D:
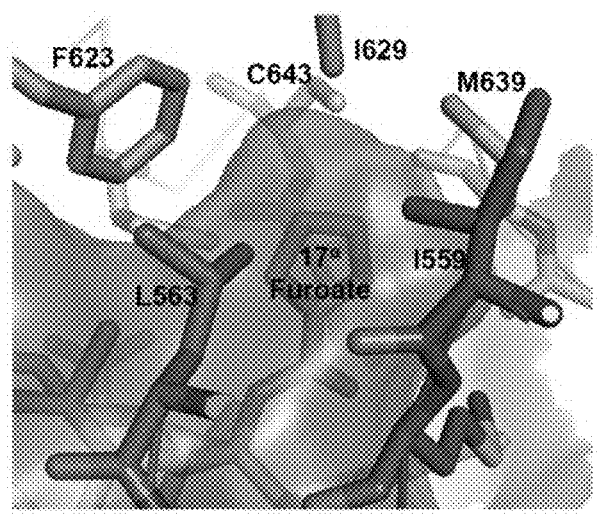

The chemical structure of DEX forms almost a flat two-dimensional surface (FIG. 4A), but in MF, the 17α furoate ester sticks out of that surface at almost 90° to the ring plane, making the ligand a three-dimensional object (FIG. 4B). In the DEX-bound GR LBD, there is an empty space above the steroid D ring, a hydrophobic cavity formed by helix 3, helix 5, the β3-β4 turn, and helix 6-7 (FIG. 4C). In the MF-bound GR LBD structure, the protruding 17α furoate expands the ligand binding pocket slightly and takes up most space of that cavity. The lipophilic 17α furoate fits nicely into the hydrophobic cavity and makes extensive hydrophobic interactions with the surrounding F623, I629, M639, C643, I559, and L563 amino acids (FIG. 4D), resembling a firmly anchored ball within a socket joint, thus explaining why MF has a 10-fold higher affinity for GR than does DEX.

Example 12: Q642 Plays a Key Role in Recognizing the Glucocorticoids of Different Potency The basic recognition of glucocorticoids by the GR LBD has been described (27, 31, 32). As in the DEX-bound GR LBD, Q570 and R611 interact with the C-3 keto group of the steroid A ring, N564 interacts with the C-11 hydroxyl group of the steroid C ring, and T739 interacts with the side chain C-21 carbonyl group (FIG. 3A). These four pairs of important hydrogen bonds hold the steroid backbone tightly in position. Relative to DEX-bound and cortisol-bound GR LBDs, the intruding C-17α furoate group of MF causes only one large change inside the ligand-binding pocket, which is the movement of Q642 in helix 7 (FIG. 5A). In the DEX-bound GR LBD structure, Q642 is perpendicular to the axis of helix 7 and forms hydrogen bonds with the C-17α hydroxyl group of DEX. Upon binding of MF, the C-17α furoate group pushes Q642 away, bending it nearly 90° into a position parallel to the axis of helix 7 (FIG. 5A).

Since the Q642 orientation is the only large change in the ligand binding packet upon binding of ME, the inventors mutated Q642 to make it smaller (Q642A), larger (Q642F), hydrophobic (Q642L), or charged (Q642E, Q642K), or to make only a slight change (Q642N). We tested those mutations using either MF or DEX at sub-saturated concentration (MF, 1 nM; DEX, 10 nM). Interestingly, for one mutation (Q642N), DEX activity was nearly abolished, while MF activity remained maximal (FIG. 5B). Thus, a single mutation could completely separate the activity of MF from that of DEX. Other mutations caused loss of most of the activity for both DEX and MF; the exception, Q642L, had half the activity with MF but no or very low activity with DEX. The 17α furcate of MF also slightly changed the conformation around M560 and M639, but mutations in those residues did not have same effect as the Q642N mutation (FIGS. 12A-B).

To analyze the prominent role of Q642 on recognizing ligands of different potency, the inventors determined full dose-response curves for MF, DEX, and cortisol—representing high, medium, and low potency, respectively—in binding to Q642N in a GR transactivation assay (FIG. 5C). For MF, the dose response curve of Q642N was indistinguishable from that of the wild type. For DEX relative to wild type, Q642N caused a large rightward shift of the curve, with the EC50 changing from 7.5 nM to 40 nM, a 5-fold decrease in potency. For cortisol, the Q642N receptor variant was inactive, even at saturation concentration. Thus, the single mutation Q642N has the ability to completely separate ligands of high, medium, and low potency, suggesting that Q642 serves as a sensor that recognizes ligands of different potency. When binding a medium- or low-potency glucocorticoid (e.g., DEX or cortisol), Q642 forms a hydrogen bond with the 17α hydroxyl group to tether the bound ligand in position within the ligand binding pocket. When binding to a highly potent ligand such as MF, Q642 is pushed away by the 17α lipophilic group. This change, coordinated with other small changes caused by ligand binding, perturbs helices 6, 6, and 7, leading to the expansion of the loop between helix 5 and helix 6 and changing the orientation of the C-terminus of the AF2 helix (FIG. 1B), resulting in the characteristics of high potency.

To investigate the exact role of Q642 in binding of different ligands, we tested the ligand binding ability of GR Q642A, for which DEX has almost no transactivation activity at a single unsaturated concentration (FIG. 5B). In an in vitro binding assay using the cytosol from AD293 cells that expressed either wild-type GR or GR Q642A, the Q642A mutant showed a substantial loss of binding affinity to DEX compared to wild-type GR (Kd (Q642A)=22.3 nM vs Kd (WT)=5.2 nM), but still retained some affinity at high ligand concentration (FIG. 13A). On the other hand, Q642A showed almost no transactivation activity, even at a saturating concentration of DEX, in a reporter assay (FIG. 13B).

These data show that the lack of DEX transactivation of GR Q642A is due to both a decrease in ligand affinity and a conformation change that inhibits GR activation. Unlike with DEX and cortisol, Q642 does not form a hydrogen bond with MF. To determine whether Q642A still has the ability to bind MF, we performed a competition binding experiment using the GR Q642A mutant protein (FIG. 13C). Both MF and cortisol were able to compete the binding of $^3$H-DEX to GR Q642A, but with a large decrease of affinity (Ki for MF and cortisol were 9 nM and 250 nM, respectively, compared to that of wild type GR at 0.7 nM and 91 nM, respectively). Taken together, these results suggest that Q642 acts as a pillar to support the ridge of helix 7 by forming a hydrogen bond with C-17α hydroxyl group-containing ligands, while pushing away ligands with a C-17α furoate group. Substituting Q642 with a small residue like alanine may lead the ridge of helix 7 to collapse and thus to lose all transactivation.

Example 13: Determination of Induction Activity

AD293 cells were transfected with 0.1 ng pRShGR, 100 ng MMTV-Luc reporter, and 10 ng TK-Renilla internal control per well in a 24-well plate. One day after transfection, cells were induced by candidate compounds at a concentration of 10 nm or 1 um (see FIG. 14). Cells were harvested and luciferase activity was measured by Promega Dual Luciferacse kit. Compound 1 shows a much lower induction activity compared to all other candidate compounds, as well as VSGC12, at the 10 nM concentration. As reported in Yuanzheng He, Jingjing Shi, Wei Yi, et al. Discovery of a highly potent glucocorticoid for asthma treatment, *Cell Discovery* (2015) 1, 15035, VSGC12 has the following chemical structure:

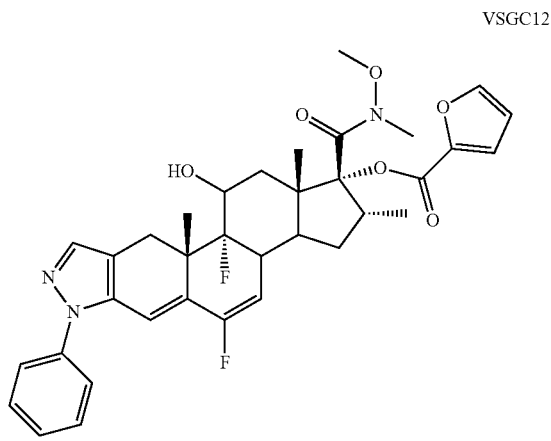

Example 14: Determination of the Anti-Inflammatory Effect

A OVA-induced mouse asthma model was used to examine the anti-inflammatory effect of candidate compounds. 7-9 weeks old Balb/c mice were primarily immunized with OVA (ovalbumin). Three weeks after the first immunization, mice were challenged with intranasal OVA, and in the meantime given different treatments (administration of ethanol or 10 nM or 1000 nM of one of the following: DEX, compound 1, compound 2, compound 3, compound 4, compound 5, compound 6, VSGC12, or FF). Related Lung (RL) function in response to acetylcholine was measured by the forced oscillation techniques with the FlexiVent system (SCIREQ). FIG. 15, a side by side comparison of FF with Compound 4 (labeled as CMPD 4) shows that Compound 4 is much more potent in repressing lung inflammation in the mouse asthma model.

Example 15: Determination of Potency and Repression of Lung Inflammation

To evaluate the potency of candidate compounds in a reporter system, an MMTV-luciferase reporter was used. The potency was measured by a full dose-response curve of candidate compounds at a various doses from 0.01 nM to 1000 nM as indicated in FIG. 16A (RLU: relative luciferase unit). Compound 4 shows a higher potency than both VSGC12 and DEX.

To evaluate the effect of candidate compounds in repressing lung inflammation, a OVA-induced mouse asthma model was used (RL: relative lung function). At the same low dose of 0.125 mg/kg, Compound 4 shows a much higher repression activity in repressing lung inflammation than VSGC12, as provided in FIG. 16B.

TABLE 3

Transient Transfection Standardization - LUC Activity in Response to Different Steroid Concentrations (illustrated in FIG. 14).

| Steroid | Conc. (nM) | Renilla | RLU | RLU/Renilla | Mean | Mean SD | Steroid Fold Induction | Fold SD | % to Dex induction | SD |
|---|---|---|---|---|---|---|---|---|---|---|
| EtOH | \ | 190,000 | 11280 | 0.059 | 0.049 | 0.010 | 1.000 | 0.199 | 3.43854525 | 0.68501624 |
|  |  | 218,400 | 8680 | 0.040 |  |  |  |  |  |  |
|  |  | 208,200 | 10160 | 0.049 |  |  |  |  |  |  |
| DEX | 10 nM | 222,600 | 151,280 | 0.680 | 0.757 | 0.073 | 15.360 | 1.487 | 52.816423 | 5.11416278 |
|  |  | 177,880 | 136,440 | 0.767 |  |  |  |  |  |  |
|  |  | 197,360 | 162,880 | 0.825 |  |  |  |  |  |  |
| CMPD 1 | 10 nM | 187,480 | 21,720 | 0.116 | 0.119 | 0.028 | 2.421 | 0.566 | 8.32635767 | 1.94486975 |
|  |  | 184,080 | 17,200 | 0.093 |  |  |  |  |  |  |
|  |  | 163,360 | 24,320 | 0.149 |  |  |  |  |  |  |
| CMPD 2 | 10 nM | 168,480 | 221,760 | 1.316 | 1.328 | 0.096 | 26.932 | 1.956 | 92.6078642 | 6.72417244 |
|  |  | 144,240 | 206,200 | 1.430 |  |  |  |  |  |  |
|  |  | 153,920 | 190,520 | 1.238 |  |  |  |  |  |  |
| CMPD 3 | 10 nM | 196,240 | 295,280 | 1.505 | 1.462 | 0.145 | 29.644 | 2.939 | 101.933403 | 10.1053848 |
|  |  | 227,320 | 295,520 | 1.300 |  |  |  |  |  |  |
|  |  | 189,440 | 299,320 | 1.580 |  |  |  |  |  |  |
| CMPD 4 | 10 nM | 189,960 | 288,320 | 1.518 | 1.332 | 0.162 | 27.026 | 3.276 | 92.9308062 | 11.264279 |
|  |  | 198,040 | 249,160 | 1.258 |  |  |  |  |  |  |
|  |  | 200,040 | 244,360 | 1.222 |  |  |  |  |  |  |
| CMPD 5 | 10 nM | 201,160 | 298,760 | 1.485 | 1.444 | 0.037 | 29.284 | 0.755 | 100.695284 | 2.59661376 |
|  |  | 185,000 | 265,160 | 1.433 |  |  |  |  |  |  |
|  |  | 176,760 | 249,760 | 1.413 |  |  |  |  |  |  |
| CMPD 6 | 10 nM | 274,080 | 353,720 | 1.291 | 1.417 | 0.166 | 28.743 | 3.370 | 98.8348855 | 11.5892314 |
|  |  | 256,280 | 347,400 | 1.356 |  |  |  |  |  |  |
|  |  | 235,840 | 378,600 | 1.605 |  |  |  |  |  |  |
| VSGC 12 | 10 nM | 197,840 | 316,240 | 1.598 | 1.402 | 0.277 | 28.433 | 5.622 | 97.767568 | 19.3299835 |
|  |  | 196,160 | 298,600 | 1.522 |  |  |  |  |  |  |
|  |  | 266,840 | 289,480 | 1.085 |  |  |  |  |  |  |
| FF | 10 nM | 218,040 | 291,040 | 1.335 | 1.367 | 0.162 | 27.730 | 3.294 | 95.3491839 | 11.3271978 |
|  |  | 200,560 | 245,360 | 1.223 |  |  |  |  |  |  |
|  |  | 183,240 | 282,800 | 1.543 |  |  |  |  |  |  |
| DEX | 1000 nM | 184,520 | 252,200 | 1.367 | 1.434 | 0.104 | 29.082 | 2.103 | 100 | 7.23156381 |
|  |  | 164,400 | 255,360 | 1.553 |  |  |  |  |  |  |
|  |  | 184,120 | 254,360 | 1.381 |  |  |  |  |  |  |
| CMPD 1 | 1000 nM | 290,600 | 186,480 | 0.642 | 0.806 | 0.159 | 16.351 | 3.225 | 56.2243432 | 11.0897089 |
|  |  | 221,200 | 180,880 | 0.818 |  |  |  |  |  |  |
|  |  | 228,840 | 219,480 | 0.959 |  |  |  |  |  |  |
| CMPD 2 | 1000 nM | 217,320 | 296,680 | 1.365 | 1.311 | 0.050 | 26.600 | 1.007 | 91.465635 | 3.46419573 |
|  |  | 233,560 | 295,960 | 1.267 |  |  |  |  |  |  |
|  |  | 248,520 | 323,600 | 1.302 |  |  |  |  |  |  |
| CMPD 3 | 1000 nM | 217,960 | 249,160 | 1.143 | 1.219 | 0.100 | 24.716 | 2.022 | 84.9885239 | 6.95223394 |
|  |  | 209,640 | 279,160 | 1.332 |  |  |  |  |  |  |
|  |  | 215,160 | 254,120 | 1.181 |  |  |  |  |  |  |
| CMPD 4 | 1000 nM | 189,200 | 222,960 | 1.178 | 1.153 | 0.023 | 23.385 | 0.466 | 80.4091951 | 1.60118417 |
|  |  | 198,680 | 225,280 | 1.134 |  |  |  |  |  |  |
|  |  | 197,360 | 226,280 | 1.147 |  |  |  |  |  |  |
| CMPD 5 | 1000 nM | 312,720 | 346,400 | 1.108 | 1.235 | 0.132 | 25.047 | 2.670 | 86.1254818 | 9.17959091 |
|  |  | 285,560 | 350,240 | 1.227 |  |  |  |  |  |  |
|  |  | 252,280 | 345,760 | 1.371 |  |  |  |  |  |  |
| CMPD 6 | 1000 nM | 227,800 | 385,840 | 1.694 | 1.614 | 0.109 | 32.739 | 2.215 | 112.573819 | 7.61748494 |
|  |  | 194,760 | 290,120 | 1.490 |  |  |  |  |  |  |
|  |  | 199,320 | 330,680 | 1.659 |  |  |  |  |  |  |
| VSGC 12 | 1000 nM | 187,600 | 331,400 | 1.767 | 1.682 | 0.146 | 34.106 | 2.961 | 117.275785 | 10.1823745 |
|  |  | 175,120 | 309,120 | 1.765 |  |  |  |  |  |  |
|  |  | 206,480 | 312,400 | 1.513 |  |  |  |  |  |  |
| FF | 1000 nM | 292,000 | 404,480 | 1.385 | 1.450 | 0.067 | 29.409 | 1.359 | 101.125138 | 4.67332455 |
|  |  | 259,720 | 394,520 | 1.519 |  |  |  |  |  |  |
|  |  | 240,680 | 347,960 | 1.446 |  |  |  |  |  |  |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims.

REFERENCES

1. Barnes P J (1998) Anti-inflammatory actions of glucocorticoids: molecular mechanisms. *Clin Sci* (Loud) 94 (6):557-572.
2. De Bosscher K, Vanden Berghe W, Haegeman G (2003) The interplay between the glucocorticoid receptor and nuclear factor-kappaB or activator protein-1: molecular mechanisms for gene repression. *Endocr Rev* 24 (4):488-522.
3. Lefstin J A, Yamamoto K R (1998) Allosteric effects of DNA on transcriptional regulators. *Nature* 392 (6679):885-888.
4. Heck S, et al. (1994) A distinct modulating domain in glucocorticoid receptor monomers in the repression of activity of the transcription factor AP-1. *EMBO J* 13 (17):4087-4095.
5. Reichardt H M, et al. (1998) DNA binding of the glucocorticoid receptor is not essential for survival. *Cell* 93 (4):531-541.
6. Rosen J, Miner J N (2005) The search for safer glucocorticoid receptor ligands. *Endocr Rev* 26 (3):452-464.
7. Schacke H, Docke W D, Asadullah K (2002) Mechanisms involved in the side effects of glucocorticoids. *Pharmacal Ther* 96 (1):23-43.
8. Stanbury R M, Graham E M (1998) Systemic corticosteroid therapy—side effects and their management. *Br J Ophthalmol* 82 (6):704-708.
9. Nakae J, Kitamura T, Silver D L, Accili D (2001) The forkhead transcription factor Foxo1 (Fkhr) confers insulin sensitivity onto glucose-6-phosphatase expression. *J Clin Invest* 108 (9):1359-1367.
10. Opherk C, et al. (2004) Inactivation of the glucocorticoid receptor in hepatocytes leads to fasting hypoglycemia and ameliorates hyperglycemia in streptozotocin-induced diabetes mellitus. *Mol Endocrinol* 18 (6):1346-1353.
11. Pinzone J J, et aL (2009) The role of Dickkopf-1 in bone development, homeostasis, and disease. *Blood* 113 (3):517-525.
12. Hoes J N, et al. (2009) Adverse events of low- to medium-dose oral glucocorticoids in inflammatory diseases: a meta-analysis. *Ann Rheum Dis* 68 (12):1833-1838.
13. Spies C M, et al. (2011) Glucocorticoids. *Best Pract Res Cl Rh* 25 (6):891-900.
14. Hoes J N, Jacobs J W, Buttgereit F, Bijlsma J W (2010) Current view of glucocorticoid co-therapy with DMARDs in rheumatoid arthritiS. *Nat Rev Rheumatol* 6 (12):693-702.
15. Frey F J, Odermatt A, Frey B M (2004) Glucocorticoid-mediated mineralocorticoid receptor activation and hypertension. *Curr Opin Nephrol Hypertens* 13 (4):451-458.
16. Simons S S, Jr. (2008) What goes on behind closed doors: physiological versus pharmacological steroid hormone actions. *Bioessays* 30 (8):744-756.
17. Wei P, et al. (1998) Modulation of hormone-dependent glucocorticoid receptor function using a tetracycline-regulated expression system. *Journal of Steroid Biochemistry and Molecular Biology* 64 (1-2):1-12.
18. Adcock I M, Nasuhara Y, Stevens D A, Barnes P J (1999) Ligand-induced differentiation of glucocorticoid receptor (GR) trans-repression and transactivation: preferential targetting of NF-kappaB and lack of I-kappaB involvement. *Br J Pharmacol* 127 (4):1003-1011.
19. Barnes P J, Adcock I M (2009) Glucocorticoid resistance in inflammatory diseases. *Lancet* 373 (9678):1905-1917.
20. Kaspers G J, et al. (1994) Glucocorticoid resistance in childhood leukemia. *Leuk Lymphoma* 13 (3-4):187-201.
21. Haarman E G, Kaspers G J L, Veerman A J P (2003) Glucocorticoid resistance in childhood leukaemia: Mechanisms and modulation. *Brit J Haematol* 120 (6):919-929.
22. Gaynon P S, Carrel A L (1999) Glucocorticosteroid therapy in childhood acute lymphoblastic leukemia. *Adv Exp Med Biol* 457:593-605.
23. Baxter J D (1976) Glucocorticoid hormone action. *Pharmacol Ther B* 2 (3):605-669.
24. Onrust S V, Lamb H M (1998) Mometasone furoate. A review of its intranasal use in allergic rhinitis. *Drugs* 56 (4):725-745.
25. McCormack P L, Plosker G L (2006) Inhaled mometasone furoate: A review of its use in persistent asthma in adults and adolescents. *Drugs* 66 (8):1151-1168.
26. Crim C, Pierre L N, Daley-Yates P T (2001) A review of the pharmacology and pharmacokinetics of inhaled fluticasone propionate and mometasone furoate. *Clin Ther* 23 (9):1339-1354.
27. Bledsoe R K, et al. (2002) Crystal structure of the glucocorticoid receptor ligand binding domain reveals a novel mode of receptor dimerization and coactivator recognition. *Cell* 110 (1):93-105.
28. Williams S P, Sigler P B (1998) Atomic structure of progesterone complexed with its receptor. *Nature* 393 (6683):392-396.
29. Simons S S (2003) The importance of being varied in steroid receptor transactivation. *Trends in Pharmacological Sciences* 24 (5):253-259.
30. Simons S S, Jr. (2006) How much is enough? Modulation of dose-response curve for steroid receptor-regulated gene expression by changing concentrations of transcription factor. *Curr Top Med Chem* 6 (3):271-285.
31. Kauppi B, Jakob C, Farnegardh M, et al. The three-dimensional structures of antagonistic and agonistic forms of the glucocorticoid receptor ligand-binding domain: RU-486 induces a transconformation that leads to active antagonism. *J. Biol Chem* 2003; 278:22748-22754.
32. Suino-Powell K, et al. (2008) Doubling the size of the glucocorticoid receptor ligand binding pocket by deacylcortivazol. *Mol Cell Biol* 28 (6):1915-1923.
33. Harmon J M, Schmidt T J, Thompson E B (1982) Non-glucocorticoid receptor-mediated effects of the potent glucocorticoid deacylcortivazol. *Cancer Res* 42 (6):2110-2114.
34. Valotis A, Hogger P (2007) Human receptor kinetics and lung tissue retention of the enhanced-affinity glucocorticoid fluticasone furoate. *Respir Res* 8:54.
35. Biggadike K, et aL (2008) X-ray crystal structure of the novel enhanced-affinity glucocorticoid agonist fluticasone furoate in the glucocorticoid receptor-ligand binding domain. *J Med Chem* 51 (12):3349-3352.
36. Bailey S (1994) The Ccp4 Suite—Programs for Protein Crystallography. *Acta Crystallogr D* 50:760-763.

37. Brunger A T, et aL (1998) Crystallography & NMR system: A new software suite for macromolecular structure determination. *Acta Crystallogr D Biol Crystallogr* 54 (Pt 5):905-921.
38. Murshudov G N, Vagin A A, Dodson E J (1997) Refinement of macromolecular structures by the maximum-likelihood method. *Acta Crystallogr D Biol Crystallogr* 53 (Pt 3):240-255.
39. He Y, et al. (2011) Identification of a lysosomal pathway that modulates glucocorticoid signaling and the inflammatory response. *Sci Signal* 4 (180):ra44.

What is claimed is:

1. A compound selected from:

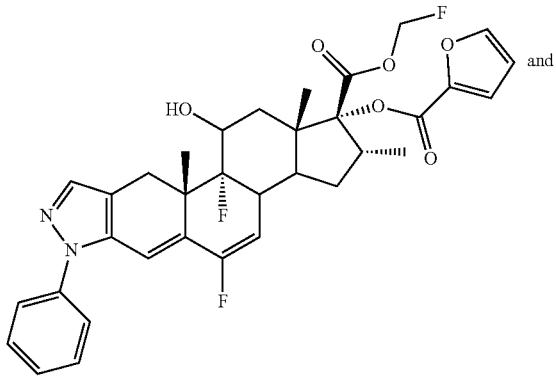

and

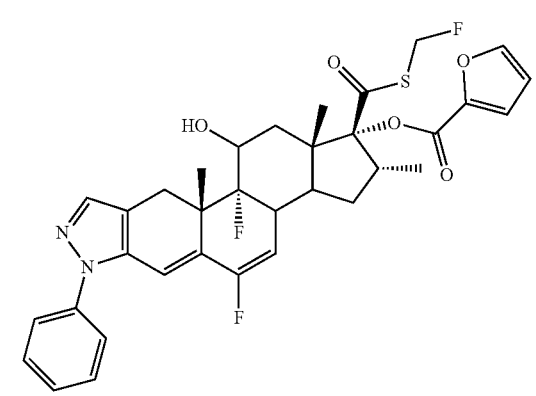

or a pharmaceutically acceptable salt thereof.

2. A pharmaceutical composition comprising the compound of claim 1, or a pharmaceutically acceptable salt thereof;

and a pharmaceutically acceptable carrier or adjuvant.

3. A method of modulating the activity of a glucocorticoid receptor in a biological sample, comprising the step of contacting the glucocorticoid receptor with a compound according to claim 1, a pharmaceutically acceptable salt thereof, or a pharmaceutical composition according to claim 2.

4. A method of treating or lessening the severity of an inflammatory disease in a patient, comprising the step of administering to the patient an effective amount of a compound according to claim 1, a pharmaceutically acceptable salt thereof, or a pharmaceutical composition according to claim 2, wherein the inflammatory disease is selected from asthma, arthritis, Crohn's disease, coeliac disease, chronic obstructive pulmonary disease, glomerulonephritis, lupus, Acne vulgaris, leukemia, and pancreatic cancer.

5. The method of claim 4, wherein the disease is selected from asthma and arthritis.

6. The method of claim 4, wherein the disease is selected from Crohn's disease and coeliac disease.

7. The method of claim 4, wherein the disease is chronic obstructive pulmonary disease.

8. The method of claim 4, wherein the disease is glomerulonephritis.

9. The method of claim 4, wherein the disease is selected from lupus and Acne vulgaris.

10. The method of claim 4, wherein the disease is selected from leukemia, and pancreatic cancer.

* * * * *

UNITED STATES PATENT AND TRADEMARK OFFICE
CERTIFICATE OF CORRECTION

Page 1 of 1

PATENT NO. : 10,954,265 B2
APPLICATION NO. : 16/341275
DATED : March 23, 2021
INVENTOR(S) : Huaqiang Eric Xu and Yuanzheng He It is certified that error appears in the above-identified patent and that said Letters Patent is hereby corrected as shown below:

In the Specification

At Column 1, Lines 18-22 after "Federal Funding.":
This invention was made with government support under DK066202 and DK071662 awarded by the National Institute of Diabetes and Digestive and Kidney Diseases/National Institutes of Health. The government has certain rights in the invention.

Should read:
This invention was made with government support under DK066202 and DK071662 awarded by the National Institutes of Health. The government has certain rights in the invention.

Signed and Sealed this
Twenty-first Day of November, 2023

Katherine Kelly Vidal
*Director of the United States Patent and Trademark Office*